US012779165B2

(12) United States Patent
Stanton et al.

(10) Patent No.: US 12,779,165 B2
(45) Date of Patent: Nov. 3, 2026

(54) ADAPTORS AND USABILITY FEATURES FOR RESPIRATORY ASSISTANCE SYSTEMS

(71) Applicant: Fisher & Paykel Healthcare Limited, Auckland (NZ)

(72) Inventors: James William Stanton, Auckland (NZ); Hamish Adrian Osborne, Auckland (NZ); Suzanne Marie Bell, Auckland (NZ); Graeme Matthew Smith, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 505 days.

(21) Appl. No.: 17/452,933

(22) Filed: Oct. 29, 2021

(65) Prior Publication Data

US 2022/0105301 A1 Apr. 7, 2022

Related U.S. Application Data

(63) Continuation of application No. 15/737,041, filed as application No. PCT/NZ2016/050098 on Jun. 16, 2016, now Pat. No. 11,191,919.

(Continued)

(51) Int. Cl.

*A61M 16/10* (2006.01)
*A61M 16/08* (2006.01)

(Continued)

(52) U.S. Cl.

CPC .... *A61M 16/1095* (2014.02); *A61M 16/0816* (2013.01); *A61M 16/0833* (2014.02);

(Continued)

(58) Field of Classification Search

None

See application file for complete search history.

(56) References Cited

U.S. PATENT DOCUMENTS 3,108,825 A 10/1963 Macdonald, Jr.
3,174,774 A 3/1965 Oetiker (Continued)

FOREIGN PATENT DOCUMENTS

CN 101132824 2/2008
CN 204307126 U 5/2015

(Continued)

OTHER PUBLICATIONS

IPRP; PCT/NZ2016/050098 Dated Dec. 19, 2017 in 16 pages.

(Continued)

*Primary Examiner* — LaToya M Louis
(74) *Attorney, Agent, or Firm* — VIA LLP

(57) ABSTRACT

A bypass adaptor for a respiratory assistance system including an inlet connector configured to connect to a gases source outlet and defining a first gases passageway with a first axis and an outlet connector configured to connect to an inspiratory conduit connector and defining a second gases passageway with a second axis, the second gases passageway being fluidly connected to the first gases passageway, the inspiratory conduit connector being incompatible with direct connection to the gases source outlet, wherein the first axis is separated from the second axis by an angle that allows the inspiratory conduit connector to be connected via the bypass adaptor to the gases source outlet in a space smaller than the length of the inspiratory conduit connector. Also provided are a port cap assembly and a humidifying apparatus including the port cap assembly, wherein the port cap assembly provides for improved assembly and/or usability.

17 Claims, 20 Drawing Sheets

Related U.S. Application Data

(60) Provisional application No. 62/295,998, filed on Feb. 16, 2016, provisional application No. 62/280,072, filed on Jan. 18, 2016, provisional application No. 62/180,518, filed on Jun. 16, 2015.

(51) Int. Cl.
*A61M 16/16* (2006.01)
*A61M 16/00* (2006.01)

(52) U.S. Cl.
CPC ........ *A61M 16/107* (2014.02); *A61M 16/109* (2014.02); *A61M 16/16* (2013.01); *A61M 16/162* (2013.01); *A61M 2016/0027* (2013.01); *A61M 16/0069* (2014.02); *A61M 2205/3368* (2013.01); *A61M 2205/3653* (2013.01); *A61M 2205/58* (2013.01)

(56) References Cited

U.S. PATENT DOCUMENTS

| | | | | |
|---|---|---|---|---|
| 3,572,660 | A * | 3/1971 | Mahon | A61M 11/06 261/78.2 |
| 3,667,463 | A * | 6/1972 | Barnes | A61M 16/16 261/DIG. 65 |
| 5,285,776 | A | 2/1994 | Bertram | |
| 6,397,841 | B1 | 6/2002 | Kenyon et al. | |
| 11,191,919 | B2 | 12/2021 | Stanton et al. | |
| 2007/0227963 | A1* | 10/2007 | Fick | B01D 35/147 210/450 |
| 2008/0054497 | A1 | 3/2008 | Bradley | |
| 2009/0078251 | A1* | 3/2009 | Zucchi | A61M 16/16 128/201.13 |
| 2010/0116272 | A1 | 5/2010 | Row et al. | |
| 2011/0156289 | A1 | 6/2011 | Steg | |
| 2012/0125333 | A1* | 5/2012 | Bedford | A61M 16/109 128/205.12 |
| 2013/0199524 | A1* | 8/2013 | Hardin | A61M 16/0875 128/202.27 |
| 2014/0158130 | A1* | 6/2014 | Coleman | A61M 16/0057 128/200.24 |
| 2014/0345614 | A1 | 11/2014 | Kwok | |
| 2015/0027204 | A1 | 1/2015 | Stoks | |
| 2016/0030697 | A1 | 2/2016 | Bigeleisen | |
| 2025/0303100 | A1 | 10/2025 | Stanton | |

FOREIGN PATENT DOCUMENTS

| | | | |
|---|---|---|---|
| EP | 1369141 | A1 | 12/2003 |
| EP | 2143459 | A1 | 1/2010 |
| WO | WO 1998/057691 | A1 | 12/1998 |
| WO | WO 2006/092001 | A1 | 9/2006 |
| WO | WO 2016/092001 | A1 | 9/2006 |
| WO | WO 2011/082221 | | 7/2011 |
| WO | WO 2013/137753 | | 9/2013 |
| WO | WO 2013/162386 | | 10/2013 |
| WO | WO 2014/144054 | A1 | 9/2014 |
| WO | WO 2015/038014 | A1 | 3/2015 |
| WO | 2016030697 | | 3/2016 |
| WO | WO 2016/186525 | | 11/2016 |

OTHER PUBLICATIONS

ISR for International App. No. PCT/NZ2016/050098, dated Oct. 17, 2016, in 14 pages.

Written Opinion for International App. No. PT/NZ2016/050098, dated Octobre 17, 2016, in 15 pages.

* cited by examiner

ADAPTORS AND USABILITY FEATURES FOR RESPIRATORY ASSISTANCE SYSTEMS

CROSS-REFERENCE TO RELATED APPLICATIONS

This application is a continuation of U.S. patent application Ser. No. 15/737,041, filed Dec. 15, 2017, entitled "ADAPTORS AND USABILITY FEATURES FOR RESPIRATORY ASSISTANCE SYSTEMS," now U.S. Pat. No. 11,191,919, which is a national stage application based on International Application No. PCT/NZ2016/050098, filed Jun. 16, 2016, entitled "ADAPTORS AND USABILITY FEATURES FOR RESPIRATORY ASSISTANCE SYSTEMS," which claims priority to U.S. Provisional Patent Application No. 62/180,518, filed Jun. 16, 2015 entitled "ADAPTORS FOR RESPIRATORY ASSISTANCE SYSTEMS," the entire contents of which are hereby incorporated by reference. This application also claims priority to U.S. Provisional Patent Application No. 62/280,072, filed Jan. 18, 2016 entitled "ADAPTORS FOR RESPIRATORY ASSISTANCE SYSTEMS," the entire contents of which are hereby incorporated by reference. This application also claims priority to U.S. Provisional Patent Application No. 62/295,998, filed Feb. 16, 2016 entitled "ADAPTORS FOR RESPIRATORY ASSISTANCE SYSTEMS," the entire contents of which are hereby incorporated by reference. Any and all applications for which a foreign or domestic priority claim is identified in the Application Data Sheet as filed with the present application are incorporated by reference in their entirety.

BACKGROUND

Technical Field

The present disclosure generally relates to respiratory assistance systems. Particular aspects of the present disclosure relate to conduit connectors and adaptors for respiratory assistance systems. Other aspects relate to respiratory assistance systems having features for improved assembly and/or usability.

Description of the Related Art

A respiratory assistance system may be used to provide respiratory gases to a patient from a gases source via an inspiratory conduit in fluid communication between the gases source and a patient interface. Examples of a patient interface may include an oral mask, a nasal mask, a full face mask covering both the nares and mouth of a patient, a nasal cannula, a tracheal mask, or an endotracheal tube. In a respiratory assistance system where the gases source is a ventilator, gases exhaled by the patient into the patient interface may be returned via an expiratory conduit in fluid communication between the patient interface and the ventilator. The inspiratory conduit and the expiratory conduit may be connected to the patient interface via a wye-piece connector.

A respiratory assistance system may include a humidification device to condition respiratory gases provided to the patient. The humidification device may include a humidification chamber containing liquid and a heater adjacent the humidification chamber to heat the liquid to produce vapor. The humidification device may be positioned in the fluid communication path between the gases source and the patient interface to heat and/or humidify respiratory gases prior to delivery via the inspiratory conduit to the patient interface. Respiratory gases delivered to a patient at 100% relative humidity and 37° C. mimic the properties resulting from the transformation of air that occurs as it passes through a person's nose to the lungs. This can promote efficient gas exchange and ventilation in the lungs, can aid defense mechanisms in the airway, and can increase patient comfort during treatment.

A respiratory assistance system that includes a humidification device may include an additional supply conduit to enable positioning of the humidification device in the fluid communication path between a patient interface and a gases source, such as a ventilator. In other words, the inspiratory conduit may connect the humidification device to the patient interface, or to a wye-piece connector that is connected to the patient interface, and the supply conduit may connect the humidification device to the ventilator. The supply conduit may connect to an inlet port of the humidification chamber, and the inspiratory conduit may connect to an outlet port of the humidification chamber.

A typical respiratory assistance system that includes a humidification device may include an inspiratory conduit having a connector that can connect either to the humidification device or to the ventilator. An inspiratory conduit having such a connector allows a user to temporarily bypass the humidification device by disconnecting the supply conduit from the ventilator and the inspiratory conduit from the humidification device and then connecting the inspiratory conduit directly to the ventilator. Temporary bypass of the humidification device may be useful for testing the ventilator and/or the inspiratory conduit prior to use or for other purposes.

The humidification chamber can include a mechanism such as float to help reduce the likelihood of the level of liquid in the chamber exceeding a particular level. The float may rise and fall with the level of liquid in the chamber. When the liquid reaches a certain level, the float may cause actuation of a mechanism, such as a valve, to obstruct or block the port that is connected to the liquid conduit to stop or slow further ingress of liquid into the chamber. The chamber can include an opening or port for the connection of a liquid conduit or feedset tube. The liquid conduit can extend from the chamber and may connect to a spike for a water bag.

A port cap assembly may be used with the humidification chamber, for example during shipping and storage. The port cap can cover the inlet port. The post of the port cap can include an extension configured to be received inside of the chamber to secure in position the float inside the chamber. The liquid conduit can be received within or held by the port cap. The spike can be received within a receptacle portion of the port cap. The port cap assembly can include a lifting structure. The lifting structure may be pivotable relative to the port cap and may comprise a ring, tab, hook or any other suitable structure. The lifting structure serves as a visual indicator to help encourage removal of the port cap while also facilitating the removal.

SUMMARY

An inspiratory conduit for use in a respiratory assistance system that includes a humidification device may have a connector including one or more components configured to mate with one or more corresponding components of the humidification device that are additions to, or modifications of, the components of a standard ventilator connector. Such a connector may support desirable features provided by the humidification device, but it may also prevent connection of the inspiratory conduit to the ventilator or to the supply conduit to temporarily bypass the humidification device.

As an example, an inspiratory conduit connector may be incompatible with a standard ventilator connector because it is configured to provide an electrical connection between the humidification device and a wire in the inspiratory conduit, such as a heater wire powered by the humidification device configured to heat the respiratory gases within the inspiratory conduit to maintain a desired temperature of the gases and/or to reduce formation of condensate in the inspiratory conduit, or a sensor wire configured to convey electrical signals to the humidification device from a sensor disposed in or near the gases flow path to measure a characteristic or property of the respiratory gases. As another example, an inspiratory conduit connector may be incompatible with a standard ventilator connector because it is configured to provide a releasably lockable connection between the inspiratory conduit and the humidification device or to prevent drainage or splashing of liquid from within the inspiratory conduit onto electrical components of the connector.

An inspiratory conduit having a connector that is incompatible with a standard ventilator connector may be connected to a ventilator to temporarily bypass the humidification device by using a first bypass adaptor. The inspiratory conduit may also be connected to a supply conduit to temporarily bypass the humidification device by using a second bypass adaptor. Each bypass adaptor may be configured to be disposable and to be retained on or attached to the inspiratory tube or other respiratory assistance system apparatus prior to and/or during use.

The humidification device may include a humidification chamber. The humidification chamber may include an inlet port for receiving relatively dry gases and an outlet port for delivering relatively moist or humid gases to a patient. The chamber can further include an opening or port for the connection of a liquid conduit or feedset tube. The liquid conduit can extend from the chamber and may connect to a spike for a water bag. The liquid conduit can be integrally formed with or permanently coupled to the chamber. The spike can be coupled to the liquid conduit via an adhesive, sonic welding, an interference fit, or any other suitable means. The spike may include a vent. If the spike is inserted into, for example, a plastic, collapsible bag, the vent may be plugged. However, if the spike is inserted into a rigid container, such as a glass bottle, the vent may be open to allow air to enter the container to help reduce or prevent negative pressures in the container. The vent can include a filter that is permeable to gases but impermeable to liquids.

In use, the liquid conduit conveys a liquid, for example, water, from a liquid source, such as a water bag, saline bag, or the like, to the chamber. The heater adjacent the chamber, such as a heater plate engaged with the base of the chamber, heats the chamber and causes at least some of the chamber contents to evaporate. The chamber can include features to help reduce the likelihood of the level of liquid in the chamber exceeding a particular level. For example, the chamber can include one or more floats. Each of the floats may rise and fall with the level of liquid in the chamber. When the liquid reaches a certain level, each of the floats may cause actuation of a mechanism to obstruct or block the port that is connected to the liquid conduit to stop or slow further ingress of liquid into the chamber. The mechanism may be a valve. Other similar features also can be used. A plurality of floats may be used, each float adapted to stop the further ingress of liquid into the chamber. To this end, a second float may provide a backup or safety mechanism in case the first float fails, thereby further reducing the likelihood of the chamber overfilling.

WO2015/174859, incorporated herein by reference, discloses various features for improving assembly and/or usability of humidification systems, including an improved cap for a port of a humidification chamber. In the arrangements described in WO2015/174859, the inlet port extends generally vertically, while the outlet port extends generally horizontally, in an elbow configuration extending from the chamber generally vertically and then generally horizontally, or in some orientation other than generally vertically. A port cap may be used to cover the inlet port during shipping and storage, for example. The port cap can include a collar and a post with the collar having a port encircling the support. The support may be a generally planar surface that includes an opening that is sized and configured to receive the inlet port, but other configurations are possible.

A retainer can extend upwardly from the support and define a forward-facing opening. The retainer can be formed by a rectangular frame that is positioned generally forward of the opening for the inlet port. The post can be inserted into the inlet port and may include a lid. The lid can overlie at least a portion of the inlet port. The lid can overlie at least a portion of the collar and may overlie the entire collar. The lid may further include a downwardly extending flange that generally enshrouds three sides of the collar. The flange may be slightly spaced from the retainer.

The post of the port cap can include a finger that may be integrally formed with the lid and configured to be received inside of the chamber to secure in position one or more floats inside the chamber. The liquid conduit can be wrapped about the inlet port. The wrapped liquid conduit can be inserted into the port cap through the forward facing opening defined by the retainer. The wrapped liquid conduit can be positioned such that the inlet port extends through the loop with the support underlying the loop. The post can be inserted into the port with the finger extending into the chamber.

The lid and the flange may generally enclose the wrapped liquid conduit. A spike can be connected to the liquid conduit. The spike can be received within a sleeve. The sleeve may be connected to the port cap, more particularly, to at least one of the collar and the post. The sleeve can be joined to, or integrally formed with, the retainer and may be pivotally connected to the collar or the retainer. The sleeve may have a flange that is connected to the retainer that extends upward from an edge of the retainer. In such configurations, the sleeve can pivot downwardly when the spike is positioned within the sleeve.

Additionally, the port cap can include a lifting structure. The lifting structure may be pivotable relative to the port cap and may comprise a ring, tab, hook or any other suitable structure. The lifting structure serves as a visual indicator to help encourage removal of the port cap while also facilitating the removal.

According to a first aspect of the present disclosure there is provided a bypass adaptor for a respiratory assistance system. The bypass adaptor is configured to enable an inspiratory conduit to be connected between a gases source and a patient interface to bypass a humidification device. A connector of the inspiratory conduit is configured to be connected to an outlet of the humidification device but is not suitable for connection to an outlet of the gases source. The bypass adaptor comprises an inlet connector, an outlet connector, and a hollow body. The inlet connector is configured to be connected to the outlet of the gases source but is not suitable for connection to the outlet of the humidification device or to the connector of the inspiratory conduit. The outlet connector is configured to be connected to the connector of the inspiratory conduit but is not suitable for connection to the outlet of the gases source or to the outlet of the humidification device. The hollow body defines a gas flow path between the inlet connector and the outlet connector. The inlet connector is different from the outlet connector in at least one physical respect such that the inlet connector includes at least one physical characteristic that enables the inlet connector to be connected to the outlet of the gases source but not to the outlet of the humidification device or to the connector of the inspiratory conduit, and/or the outlet connector includes at least one characteristic that enables the outlet connector to be connected to the connector of the inspiratory conduit but not to the outlet of the gases source or to the outlet of the humidification device.

The shape of the inlet connector may be different from the shape of the outlet connector. Each of the inlet connector and the outlet connector may be tubular. Each of the inlet connector and the outlet connector may include an external diameter and an internal diameter. One or both of the external diameter and the internal diameter of the inlet connector may be different from the respective external diameter or the internal diameter of the outlet connector.

The length of the inlet connector may be different from the length of the outlet connector. At least one of the inlet connector and the outlet connector may taper along its length. Each of the inlet connector and the outlet connector may be tapered. The taper on the inlet connector may be different to the taper on the outlet connector.

In some embodiments, each of the inlet connector and the outlet connector may be elongate and have a respective longitudinal axis, and the longitudinal axis of the inlet connector may be aligned with the longitudinal axis of the outlet connector. The longitudinal axis of the inlet connector may be parallel with the longitudinal axis of the outlet connector. The longitudinal axis of the inlet connector may be coaxial with the longitudinal axis of the outlet connector.

In some embodiments, each of the inlet connector and the outlet connector may be elongate and have a respective longitudinal axis, and the longitudinal axis of the inlet connector may not be aligned with the longitudinal axis of the outlet connector. The longitudinal axis of the inlet connector may be inclined relative to the longitudinal axis of the outlet connector. The longitudinal axis of the inlet connector may be at an obtuse angle relative to the longitudinal axis of the outlet connector. The angle separating the longitudinal axis of the inlet connector from the longitudinal axis of the outlet connector may be between about 110 degrees and about 160 degrees. The angle separating the longitudinal axis of the inlet connector from the longitudinal axis of the outlet connector may be between about 110 degrees and about 145 degrees. The angle separating the longitudinal axis of the inlet connector from the longitudinal axis of the outlet connector may be about 112 degrees.

The bypass adaptor may comprise a retainer configured to retain the bypass adaptor on or to another component of the respiratory assistance system. The retainer may be a conduit retainer configured to retain the bypass adaptor on or to a conduit of the respiratory assistance system. The conduit retainer may comprise a ring through which the conduit is received. The conduit retainer may comprise a spring clip defining a variable size mouth configured to receive the conduit. The mouth may be biased to a condition in which the mouth retains the conduit. The spring clip may be of horseshoe shape.

Each of the inlet connector and the outlet connector may be at a respective end of the housing. A notional straight line between the ends of the housing may be shorter than the length of the gas flow path through the housing. One end of the housing may be vertically spaced from the other end of the housing when the housing is viewed from the side. The gases source may be a ventilator.

According to a second aspect of the present disclosure, there is provided a bypass adaptor for a respiratory assistance system. The bypass adaptor comprises a source plug and an inspiratory plug. The source plug is configured to connect to a gases source outlet. The source plug defines a first gases passageway with a first axis. The inspiratory plug is configured to connect to a connector of an inspiratory conduit. The inspiratory plug defines a second gases passageway with a second axis. The second gases passageway is fluidly connected to the first gases passageway. The connector of the inspiratory conduit is incompatible with direct connection to the gases source outlet.

According to a third aspect of the present disclosure, there is provided a conduit kit for a respiratory assistance system. The conduit kit comprises an inspiratory conduit configured to be connected between a patient interface and a humidification device and the bypass adaptor of the first or second aspects of the present disclosure.

The conduit kit may comprise a supply conduit configured to be connected between a gases source and the humidification device. The conduit kit may comprise an interface connector configured to form a connection between an end of the inspiratory conduit and the patient interface. The interface connector may comprise a wye-piece. The conduit kit may comprise an expiratory conduit.

According to a fourth aspect of the present disclosure, there is provided a respiratory assistance system comprising a gases source, a humidification device, an inspiratory conduit, and the bypass adaptor of the first or second aspects of the present disclosure. The gases source and the humidification device are configured to be connected by a supply conduit. The inspiratory conduit is configured to be connected between the humidification device and a patient interface. The bypass adaptor is configured to enable the inspiratory conduit to be connected between the gases source and the patient interface to bypass the humidification device.

According to a fifth aspect of the present disclosure, a bypass adaptor comprises a source plug configured to connect to a gases outlet port and defining a first gases passageway with a first axis and an inspiratory plug configured to connect to an inspiratory conduit connector and defining a second gases passageway with a second axis, the second gases passageway being fluidly connected to the first gases passageway, the inspiratory conduit connector being incompatible with direct connection to the gases outlet port, wherein the first axis is separated from the second axis by an angle that allows the inspiratory conduit connector to be connected via the bypass adaptor to the gases outlet port in a space smaller than the length of the inspiratory conduit connector.

The angle separating the first axis from the second axis can be between about 110 degrees and about 160 degrees. The angle separating the first axis from the second axis can be between about 110 degrees and about 145 degrees. The angle separating the first axis from the second axis can be about 112 degrees. The bypass adaptor can comprise a tube retainer configured to attach the bypass adaptor to a tube. The tube retainer can comprise a ring. The tube retainer can comprise a horseshoe.

According to a sixth aspect of the present disclosure, a bypass adaptor comprises a source plug configured to connect to a supply conduit connector and defining a first gases passageway and an inspiratory plug configured to connect to an inspiratory conduit connector and defining a second gases passageway, the second gases passageway being fluidly connected to the first gases passageway, the inspiratory conduit connector being incompatible with direct connection to the supply conduit connector.

The bypass adaptor can comprise a tube retainer configured to attach the bypass adaptor to a tube. The tube retainer can comprise a ring. The tube retainer can comprise a horseshoe, more particularly, a horseshoe-shaped or generally C-shaped member.

According to a seventh aspect of the present disclosure, a port cap assembly is configured to cover a port, preferably an inlet port, of a humidification chamber for shipping and/or storage, the port cap assembly comprising a port cap having a first wall portion and a second wall portion, the first and second wall portions being fixedly positioned relative to one another and each of the first and second wall portions having an aperture therethrough to define a passageway through the wall portions; wherein the passageway is configured to receive a leg therethrough that extends into the port when the port cap is engaged with the port, wherein at least one of the apertures in the first and second wall portions is arranged and/or configured to control an orientation of the leg relative to the port. According to preferred embodiments, the leg forms a part of the port cap assembly.

The port cap may comprise one or more additional wall portions or members that prevent or block insertion of the leg in in at least one orientation and/or allow insertion of the leg in only one or more predetermined orientations. To achieve this, the one or more wall portions or members may together form a lattice across at least a part of the passageway. Alternatively, a wall may extend across at least a portion of the passageway and/or one or more openings may be provided therein. These openings or spacings define access pathway(s) for the leg through the passageway and when engaged with a chamber port, into the chamber to engage and retain one or more floats. According to some embodiments, the openings may have a shape that is complementary to a transverse cross-section of the leg.

The at least one orientation and/or the one or more predetermined orientations may be a rotational orientation of the leg about an axis extending through the passageway and/or relative to the port.

The port cap assembly may comprise a flange extending away from the second wall portion that defines a rim. Additionally or alternatively, the port cap assembly may comprise a lid configured to engage the port cap and/or the leg and/or a wall defining the port. Preferably retaining means are provided such that the lid is prevented, at least in part, from being inadvertently detached from the port cap. For example, a bump or friction fit may be provided between at least a part of the lid and a surface of the port assembly that engages the lid when the lid is in a closed position so as to cover the chamber port, preventing dust etc from entering the chamber. For example, the lid may be configured to releasably engage the rim and/or the or at least one of the one or more additional wall portions. To enable easy removal of the assembly from a chamber port, preferably the force required for disengagement is low such that little resistance is met when a user removes the assembly by hand. This is particularly important in that some users may have limited dexterity or use of their hands or fingers.

The port cap assembly may comprise a skirt or downwardly depending wall configured to extend about at least a part of an outer perimeter of the first and/or second wall portions. This can provide for a cleaner or neater appearance as well as providing for integrity of the assembly and/or aiding in preventing the ingress or foreign material into the chamber.

The leg may be joined to the lid and/or a pull tab or ring. The lid may comprise a weakened portion that is configured to be visibly damaged when a user removes the lid from the port.

The wall portions can be configured to define the passageway so as to be substantially aligned with the port, said controlled orientation of the leg comprising alignment of the leg inside the port. This may be provided for by both the first and second wall portions being arranged and/or configured to control an orientation and/or position of the leg relative to the port. The alignment may be such that the leg is substantially parallel to the chamber port. Thus the passageway may control the orientation of the leg about at least 2 degrees of freedom, these being rotationally about two perpendicular axes, each of these being perpendicular to the passageway (and to the inlet port when the port cap and leg are coupled thereto).

The port cap assembly can include other or additional orientation and/or alignment features. According to one embodiment, the port cap includes one or more projections or recesses that engage one or more corresponding recesses or projections associated with the port (preferably provided on an external wall thereof) so as to control a rotational orientation of the port cap relative to the port about an axis through the passageway. Additionally or alternatively, the lid of the port cap can be configured to engage the leg. For example, one or more projections or recesses provided on the lid may engage one or more corresponding recesses or projections on the leg to control a position and/or orientation thereof. According to some embodiments, the recesses or projections on the lid may be configured to additionally or alternatively engage a wall defining the leg without separate or additional means provided on the leg to enable engagement. Where the leg comprises a generally cylindrical portion that the lid engages, the lid may be provided with a projection configured to fit snugly inside or outside of the cylindrical portion.

Additionally or alternatively, an opening or some other part of the passageway may be configured to control a position and/or orientation of the leg relative to the port cap. According to such embodiments, the port cap and/or the leg may comprise orientation features for cooperating with the port so as to further control an orientation of the leg with respect to the port.

According to such embodiments, at least some part of the passageway may be configured to define an opening at least partially complementary to a section of the leg. For example, by way of non-limiting example, the leg may have an arcuate section with the passageway defining an opening complementary to that section. Thus, a position of the leg inside the passageway may be controlled, as may a rotational orientation of the leg about a longitudinal axis of the passageway. Preferably, the leg has a non-planar and/or non-symmetrical cross-section so as to limit rotational orientation about an axis through the passageway to a single orientation.

As will be appreciated, only parts of the perimeter of the section of the leg may be engaged by the walls defining the passageway. For example, a lattice may be provided comprising one or more sections extending at least part way across the passageway, the lattice defining a location in which the leg may be inserted and preventing insertion elsewhere, and further controlling a rotational orientation of the leg relative to the port cap about an axis through the passageway.

To aid insertion of the leg into the passageway during initial assembly, preferably, the complementary opening of the port cap may be positioned at or proximate to (but preferably on the side distal from the first wall portion), thereby providing a visual clue as to where the leg should be inserted.

More than one such complementary opening may be provided. For example, both the first and second, or other, wall portions may define an opening at least partially complementary to a section of the leg, thereby also controlling an orientation of the leg about perpendicular axes, each being perpendicular to the axis of the passageway.

Throughout the specification, reference to an axis of the passageway is not intended to limit the passageway to having any rotational symmetry. For example, the passageway may have a square, triangular, L-shaped etc. profile. Rather it is intended to relate to a length of the passageway.

Note that the walls and/or members used to define the restricted passageway may be integral with, or an insert in, another part of the port cap assembly or the port. Thus, another aspect of the invention provides for such insert.

The leg can additionally or alternatively include orientation and/or alignment features, and or intrinsically provide therefor. According to one embodiment, at least a portion of the leg is dimensioned so as to fit snugly inside the port, thereby controlling an alignment of the leg with respect to the inlet port. Additionally or alternatively, the leg can include one or more projections or recesses that engage one or more corresponding recesses or projections associated with the inlet port (preferably provided on an internal wall thereof) so as to control a rotational orientation of the leg relative to the inlet port about an axis through the passageway.

The leg can be configured to secure one or more floats within the chamber for shipping and/or storage. To this end, the leg may define or have one or more engagement points, each engagement point being configured to engage a respective float.

According to some embodiments, the leg comprises a cylindrical portion at or near a first end which tapers towards the second end by portions of the cylinder effectively being cut away or removed and/or the diameter of the cylinder reducing towards the second end. Preferably the cylindrical portion is hollow such that the first end of the leg is open. Tapering can aid insertion of the leg through the passageway and into the inlet port of the chamber. Cut-outs and the like perform a similar function but can also assist in enabling proper insertion of the leg into the chamber such that that the required engagements with the float(s) are effected. Further, cut-outs and/or reduced dimensions of at least parts of the leg can reduce the likelihood of potential damage to features inside the chamber such as sensors or grommets provided therefor. Controlling orientation of the leg can serve a similar function.

According to some embodiments, the chamber may include a baffle that defines an arcuate profiled passageway inside the chamber, the arcuate profile being complementary to the profile of the portion of the leg that passes therethrough when the port cap assembly (e.g. a port and a leg) are engaged with the inlet port of the humidification chamber. By forming the leg profile to be complementary to the arcuate passageway, the leg and arcuate passageway can cooperate to control a rotational position of the leg inside the inlet. Further, the baffle can assist in preventing liquid in the chamber from spilling as the chamber is transported and further controls flow of gases into the chamber, providing for more effective humidification.

The leg can include a gripping portion and may be in the form of a ring, tab or hook. The gripping portion can be integrally formed with, or joined to the leg. According to some embodiments, the gripping portion is joined to the leg via an arm. The arm can be joined to the leg at or proximate to the first end thereof. The gripping portion can be configured to facilitate removal of the leg from the chamber.

According to some embodiments, the gripping portion and/or the arm may be used or include features that enable an orientation of the leg to be controlled relative to the port cap. For example, the lid can include a projection or recess that engages a portion of the gripping portion or the arm such that it is inhibited from rotating about an axis through the passageway. According to some embodiments, this can be realised by including a raised or step portion in the lid, or a cut-away from the rim or the lid, such that there is a space within which the arm or an engaging part of the gripping portion is able to be snugly accommodated with little or no lateral movement of the arm then possible.

It will be appreciated that various ones of the orientation/alignment features may cooperate to ease assembly and retain the assembly in a desired configuration.

The lid can be connected to a main body of the port cap via a hinge. This hinge may be in the form of a flexible arm of, for example, polymer-based material that is integrally formed with or fixedly joined to the lid and the main body of the port cap, preferably at or proximate the rim. The flexible arm may comprise a weakened portion to enable the lid to be detached from other parts of the assembly. By configuring the lid to be able to engage the port, it can act as a cover for the port so as to prevent or at reduce ingress of foreign material into the chamber.

The lid can further comprise a projection that engages the inside or outside of the rim to provide for improved connection and retention of the lid in a closed position of engagement on the main body.

The port cap assembly can further comprise a sleeve for receiving and removably retaining a spike which may be provided with a water or other humidifying agent feedset. For example, the spike may be coupled or couplable to a delivery conduit that is coupled or couplable to the humidification chamber. According to some embodiments, the sleeve can be connected to a main body of the port cap, preferably at or adjacent the rim.

The port cap can further include a joining wall extending between the first and second wall portions, preferably at or near the perimeters or edges of the wall portions. The joining wall preferably extends beyond the second wall portion to provide said flange and rim. At least one opening or window can be provided in the joining wall such that the joining wall does not extend completely about the perimeters or edges of the wall portions. When the leg is assembled or engaged to the port cap, the joining wall, the first and second wall portions and a portion of the leg can define a space for accommodating at least a portion of flexible tubing for use in a humidifying agent feedset. More particularly, according to some embodiments, at least one end of feedset tubing coils may be received in said space with the leg then being inserted into the passageway to retain the coils in position. A portion of the coils may extend out through the opening or window such that the coils wrap about the leg.

According to an eighth aspect of the present disclosure, an insert for a port, preferably an inlet port, of a humidification chamber for use with the port cap assembly of the seventh aspect. The insert may comprise one or more wall portions that define a passageway that prevent or block insertion of a leg of the port cap assembly into said port in at least one orientation and/or allow insertion of the leg in only one or more predetermined orientations. The one or more wall portions may define a lattice configured to extend across at least a part of the port, in use.

The at least one orientation and/or the one or more predetermined orientations may be a rotational orientation of the leg about an axis extending through the port. The insert may include one or more orientation and/or alignment features that are configured to cooperate with one or more corresponding orientation and/or alignment features in or about the port so as to control or define an orientation and/or position of the insert relative to the port. The one or more orientation and/or alignment features may control a rotational orientation of the insert relative to an axis extending through the port.

According to an ninth aspect of the present disclosure, a leg of a port cap assembly, configured to be used with the port cap assembly of the seventh aspect and/or the insert of the eighth aspect. Other features of the leg may, for example, be taken from the disclosure provided in respect of the seventh aspect.

According to a tenth aspect of the present disclosure, a humidification apparatus comprising a humidification chamber configured to engage the port cap assembly of the seventh aspect and/or the insert of the eighth aspect and/or the leg of the ninth aspect.

In addition to the inlet port of the chamber being configured to receive the leg therein and the port cap thereabout, one or more orientation or alignment features may be provided on or about the inlet port to cooperate with one or more the orientation or alignment features of the port cap assembly specified above with regards the seventh aspect. For example, one or more or projections, recesses, grooves and ribs may be provided on an internal or external wall of or associated with the inlet port of the chamber.

The humidification apparatus can further comprise any one or more of one or more floats, a baffle defining an arcuate passageway inside a portion of the chamber, a feedset assembly, an inspiratory tube, an expiratory tube, and a patient interface. The feedset assembly can include a liquid conduit and a spike or some other means for coupling to a humidifying agent reservoir.

For purposes of summarizing the disclosure and the advantages achieved over the prior art, certain objects and advantages are described herein. It is to be understood that not necessarily all such objects or advantages need to be achieved in accordance with any particular embodiment. Thus, for example, those skilled in the art will recognize that the disclosure may be embodied or carried out in a manner that achieves or optimizes one advantage or group of advantages as taught or suggested herein without necessarily achieving other objects or advantages as may be taught or suggested herein. All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other aspects of the present disclosure will be described with reference to the following drawings, which should be considered illustrative but not limiting.

DETAILED DESCRIPTION

Figure 1:
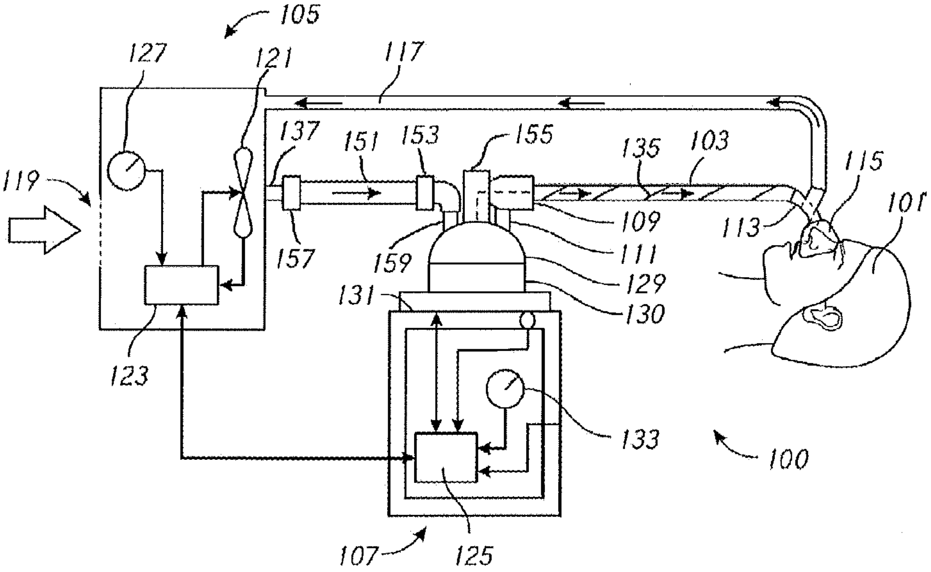
FIG. 1 is a diagram of an example respiratory assistance system that includes a gases source such as a ventilator and a humidification device.

FIG. 1 is a diagram of an example respiratory assistance system 100 that may be used to provide respiratory gases to a patient 101. The respiratory assistance system 100 may comprise a gases source 105 in fluid communication with a patient interface 115 via an inspiratory conduit 103 and an expiratory conduit 117. The inspiratory conduit 103 and the expiratory conduit 117 may be connected to the patient interface 115 via a wye-piece connector 113. In some configurations, the gases source 105 comprises a ventilator. In some configurations, the gases source 105 comprises a fan 121 configured to draw air or other gases through an inlet 119 and deliver the air or other gases through a source outlet 137. In some configurations, the inspiratory conduit 103 may be connected to the source outlet 137 (not shown). An electronic controller 123 may control a speed of the fan 121 in response to input to the electronic controller 123, including but not limited to user input supplied via a user interface 127. The electronic controller 123 may also comprise, or be arranged to be controlled by, predetermined control algorithms that control the fan speed based on predetermined methodologies and/or based on data inputs from suitable sensors within the respiratory assistance system 100.

In the configuration shown, the respiratory assistance system 100 also comprises a humidification device 107 that is configured to condition respiratory gases provided to the patient 101. The humidification device 107 may be positioned in the fluid communication path between the ventilator 105 and the patient interface 115 to heat and/or humidify respiratory gases prior to delivery via the inspiratory conduit 103 to the patient interface 115. The humidification device 107 comprises a humidification chamber 129 that contains a liquid 130 and a heater 131 adjacent to the humidification chamber 129 to heat the liquid 130 to produce vapor that humidifies respiratory gases passing over the liquid 130. In some configurations, the inspiratory conduit 103 comprises a heater wire 135 configured to maintain a temperature of gases delivered through the inspiratory conduit 103 to the patient interface 115 and to reduce formation of condensate in the inspiratory conduit 103. An electronic controller 125 may control a duty cycle of the heater 131, a duty cycle of the heater wire 135, and/or at least a portion of the function of the electronic controller 123, in response to input to the electronic controller 125, including but not limited to user input supplied via a user interface 133. In some configurations, the electronic controller 123 may control at least a portion of the function of the electronic controller 125.

The humidification device 107 may be connected to the ventilator 105 by a supply conduit 151. In particular, a source connector 157 of the supply conduit 151 may be connected to the source outlet 137, and a humidification device connector 153 of the supply conduit 151 may be connected to an inlet port 159 of the humidification chamber 129. An inspiratory connector 109 of the inspiratory conduit 103 may be connected to an outlet port 111 of the humidification chamber 129, so that gases delivered to the humidification chamber 129 from the ventilator 105 through the supply conduit 151 can continue on through the inspiratory conduit 103 to the patient interface 115. In some configurations, the inspiratory connector 109 may be configured to be connected to a mounting portion 155 of the humidification device 107, so that electrical signals can pass from the humidification device to the inspiratory conduit 103 through an electrical connection provided by the inspiratory connector 109. As an example, but without limitation, the electronic controller 125 may control the duty cycle of the heater wire 135 via the electrical connection provided by the inspiratory connector 109.

Figure 2:
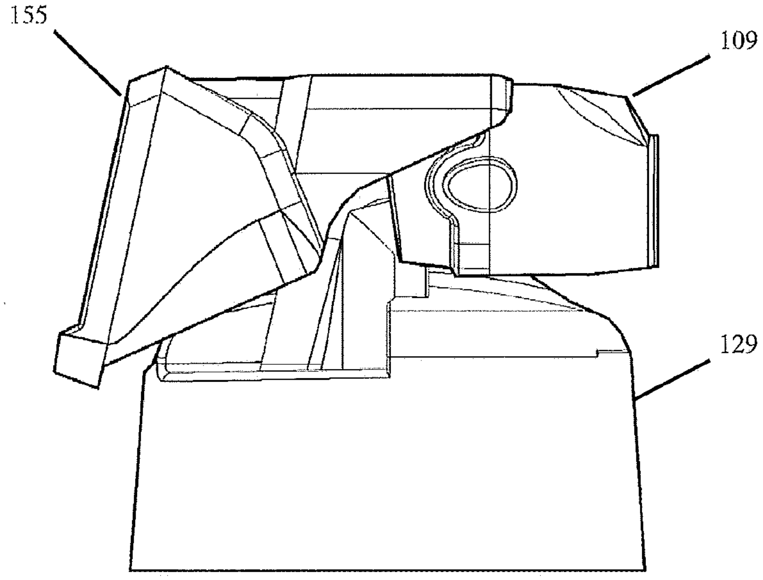
FIGS. 2-4 are perspective views of a humidification chamber mounted on a mounting portion of the humidification device.
Figure 3:
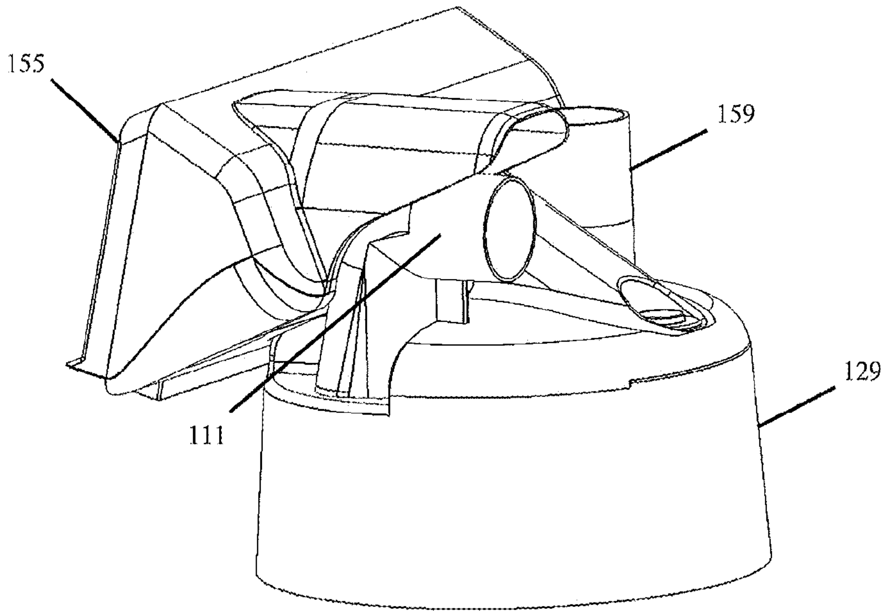
Figure 4:
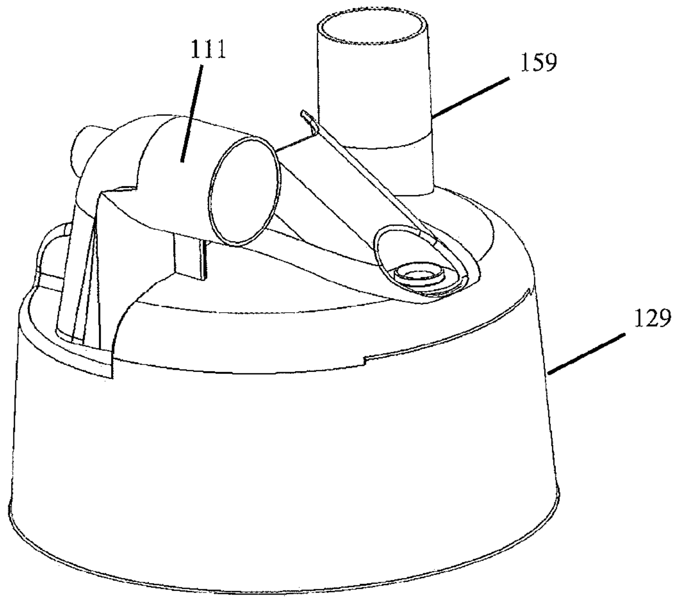
Figure 5:
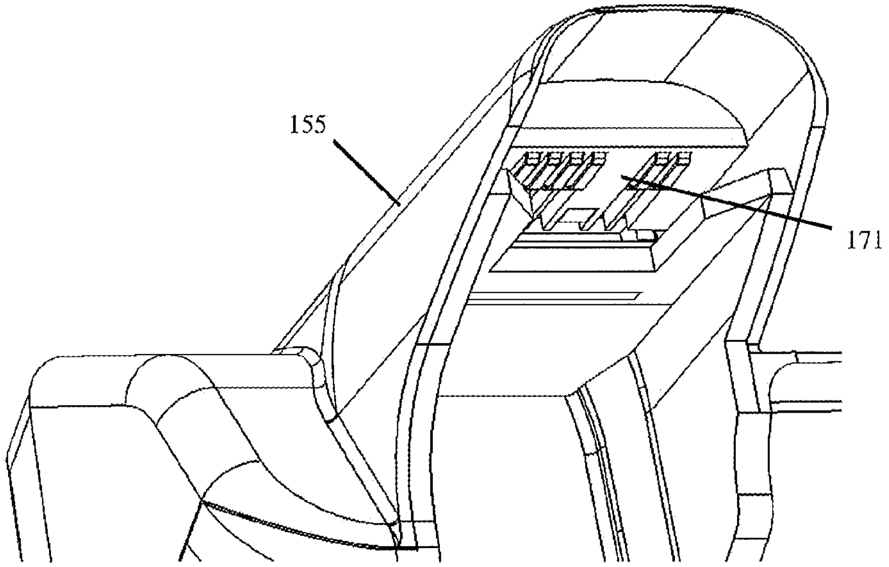
FIG. 5 is a perspective view of a mounting portion of a humidification device.
Figure 6:
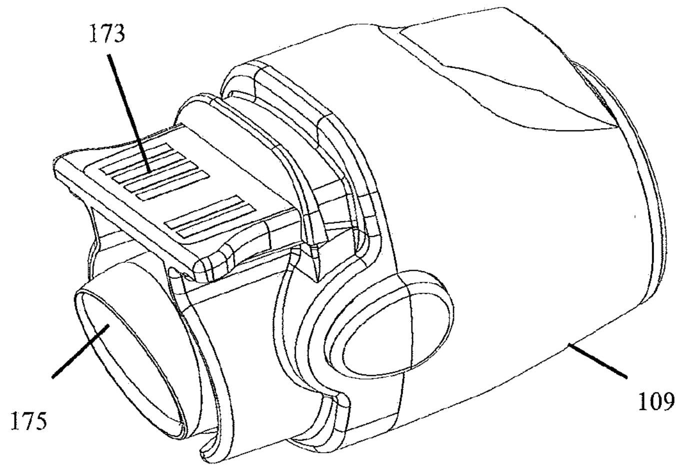
FIG. 6 is a perspective view of an inspiratory conduit connector.

FIGS. 2 to 6 show various views of an example embodiment of the inspiratory connector 109 that is configured to provide an electrical connection to the mounting portion 155 of the humidification device 107 and a gases connection to the outlet port 111 of the humidification chamber 129. FIG. 2 is a side view of the inspiratory connector 109 connected to the mounting portion 155 and to the humidification chamber 129. FIG. 3 shows the humidification chamber 129 positioned adjacent to the humidification chamber 129 in the same manner as in FIG. 2, but with the inspiratory connector 109 not present. A port plug 175 of the inspiratory connector 109, shown in FIG. 6, may be configured to be positioned within the outlet port 111 of the humidification chamber 129, shown in FIGS. 3 and 4, when the inspiratory connector 109 is connected to the humidification chamber 129. An electrical terminal 173 of the inspiratory connector 109, shown in FIG. 6, may be configured to mate with an electrical terminal 171 of the mounting portion 155, shown in FIG. 5, when the inspiratory connector 109 is connected to the mounting portion 155.

It may be desirable to connect the inspiratory conduit 103 directly to the ventilator 105, temporarily bypassing the humidification device 107, to test the ventilator 105 and/or the inspiratory conduit 103 or for other purposes. In some configurations, the humidification device 107 may be bypassed by disconnecting the source connector 157 of the supply conduit 151 from the source outlet 137, disconnecting the inspiratory connector 109 from the outlet port 111 of the humidification chamber 129, and connecting the inspiratory connector 109 directly to the source outlet 137.

However, in some embodiments, the inspiratory connector 109 may be configured to connect to the outlet port 111 and to the mounting portion 155 of the humidification device 107 in a manner that prevents the inspiratory connector 109 from connecting directly to the source outlet 137. In particular, the port plug 175 of the inspiratory connector 109 may comprise a size and/or shape that is compatible with the outlet port 111 of the humidification chamber 129 but is not compatible with the source outlet 137. For example, the inspiratory connector 109 may comprise retention features configured to provide a releasably lockable connection between the inspiratory connector 109, the humidification chamber 129, and the mounting portion 155 that may prevent, or at least fail to sufficiently provide, appropriate retention to the source outlet 137. Example embodiments of such retention features are disclosed in PCT/NZ2014/050024, filed on 19 Dec. 2014, and published as WO/2015/093989 and which is hereby incorporated by reference in its entirety.

Figure 7:
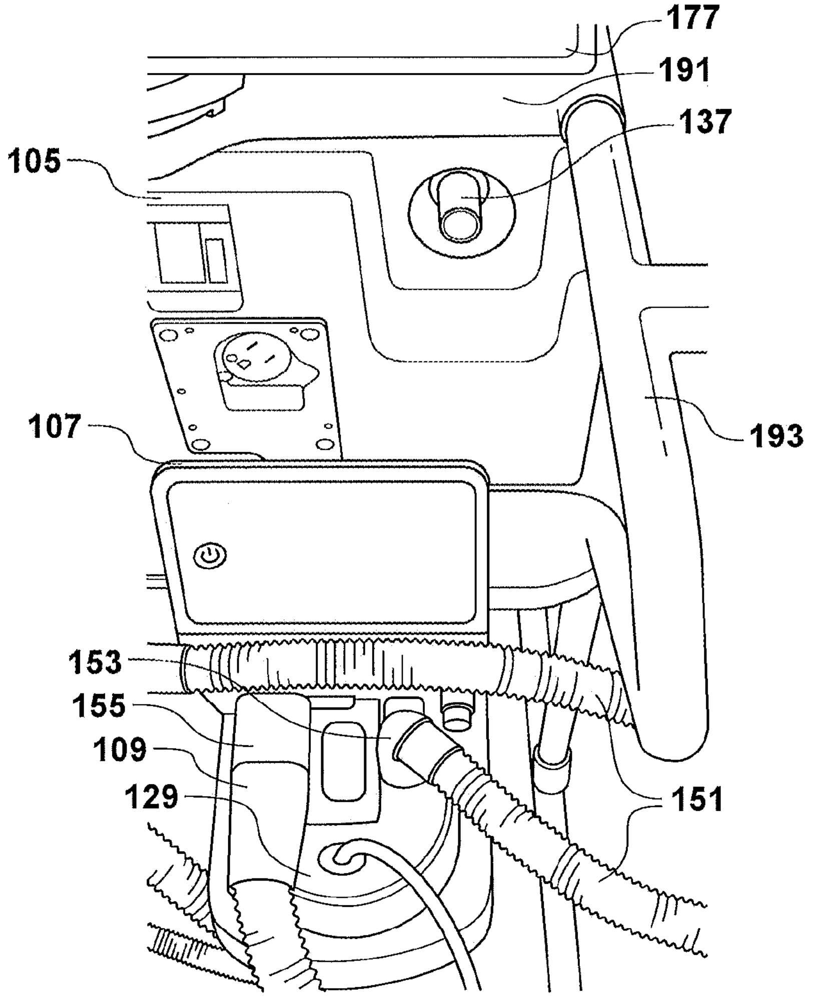
FIGS. 7-11 are photographs of various aspects of a ventilator, and a humidification device mounted in close proximity to the ventilator.

FIG. 7 is a photograph of an example embodiment of the ventilator 105 and the humidification device 107, with the humidification device 107 in close proximity to the ventilator 105 in a typical mounting arrangement. The inspiratory connector 109 is shown connected to the mounting portion 155 and to the outlet port 111 of the humidification chamber 129. The humidification device connector 153 of the supply conduit 151 is shown connected to the humidification chamber 129 at the inlet port 159. The source outlet 137 as shown is exposed; however, the source connector 157 of the supply conduit 151 may be attached to the source outlet 137 in use.

Figure 8:
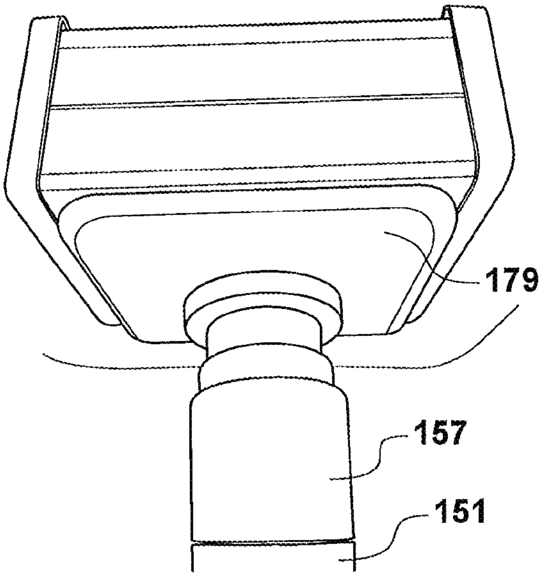
Figure 9:
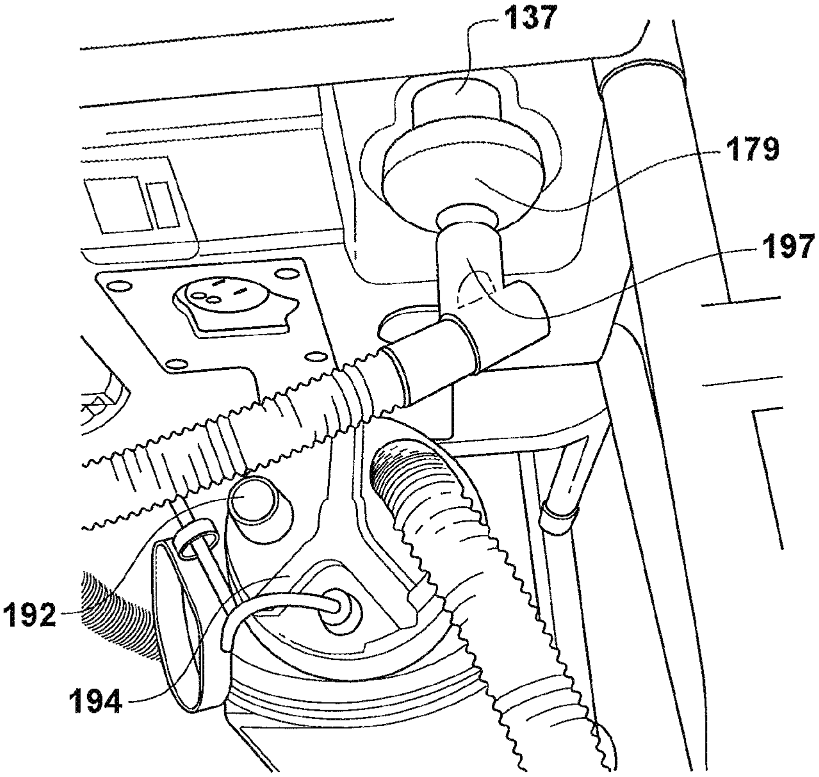

In some configurations, as illustrated in FIG. 8, a filter 179 is positioned inline between the supply conduit 151 and the source outlet 137; in other words, the filter 179 may be connected to the source outlet 137, and the source connector 157 of the supply conduit 151 may be connected to the filter 179. FIG. 9 shows an alternate embodiment of the filter 179 connected between the source outlet 137 and an older inspiratory connector 197. The older inspiratory connector 197 is configured to attach to either the source outlet 137, the filter 179, or an outlet port 192 of an older humidification chamber 194.

Figure 10:
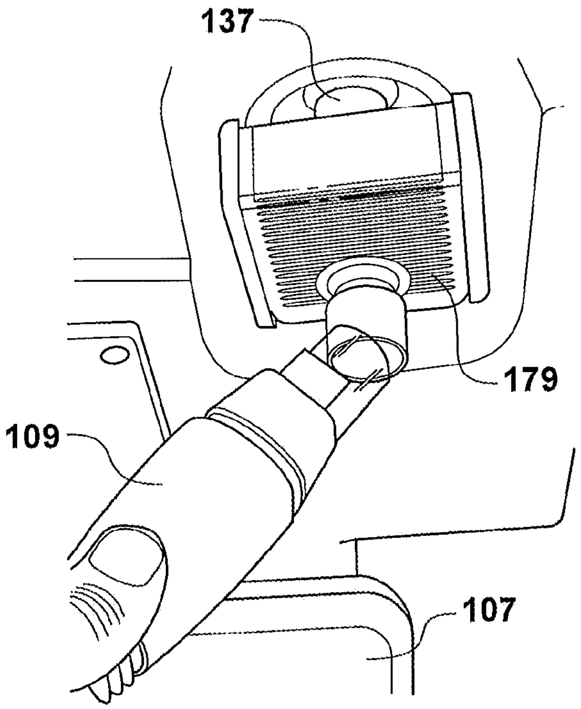
Figure 11:
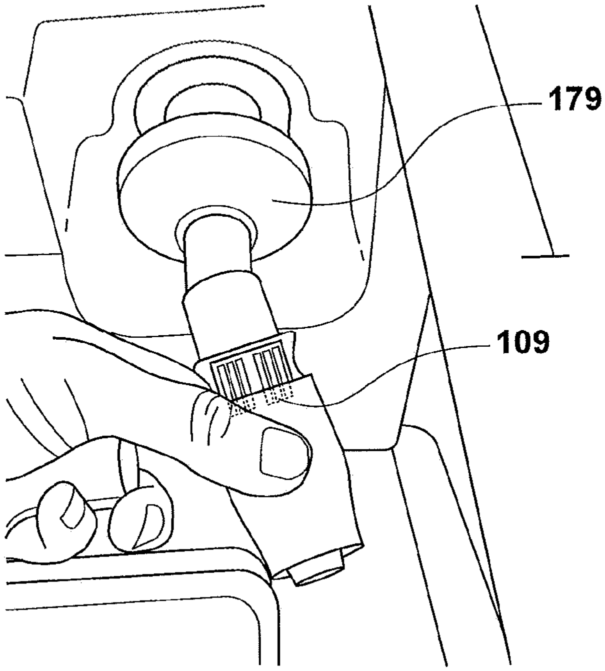

The typical mounting arrangement depicted in FIG. 7 of the humidification device 107 in close proximity to the ventilator 105 may also contribute to the incompatibility of the inspiratory connector 109 with direct connection to the source outlet 137. For example, the inspiratory connector 109 may be too large to fit into the gap between the humidification device 107 and the source outlet 137. FIGS. 10 and 11 show examples of a user attempting to connect various embodiments of the inspiratory connector 109 to various embodiments of the filter 179. Examples of physical constraints created by a typical mounting arrangement of the humidification device 107 in close proximity to the ventilator 105 are illustrated in FIGS. 12 and 13.

Figure 12:
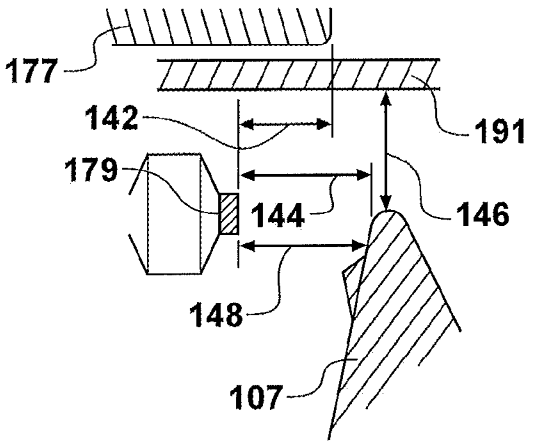
FIGS. 12-13 are part sectional side views illustrating example dimensions of gaps between various aspects of a ventilator and a humidification device mounted in close proximity to the ventilator.

FIG. 12 is a side view of an example arrangement of the humidification device 107 in close proximity to the filter 179 attached to the source outlet 137, showing a gap 144 between an upper portion of a rear edge of the humidification device 107 and a front edge of the filter 179 of about 79 mm and a gap 148 between a lower portion of the rear edge of the humidification device 107 and the front edge of the filter 179 of about 76 mm. FIG. 10 also shows a gap 142 between the front edge of the filter 179 and a front edge of a ventilator user interface housing 177 of about 40 mm and a gap 146 between a top edge of the humidification device 107 and a bottom edge of a ventilator rear handle bar 191 of about 95 mm.

Figure 13:
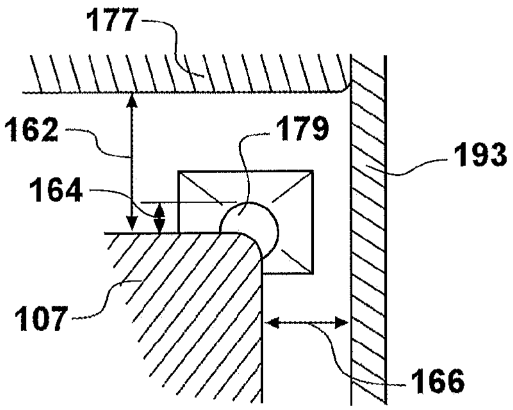

FIG. 13 is a front view of an example arrangement of the humidification device 107 in close proximity to the filter 179 attached to the source outlet 137, showing a gap 164 between a top edge of the humidification device 107 and a top edge of the filter 179 of about 10 mm. FIG. 11 also shows a gap 162 between the top edge of the humidification device 107 and a bottom edge of the ventilator user interface housing 177 of about 160 mm and a gap 166 between a side edge of the humidification device 107 and a side edge of a ventilator side handle bar 193 of about 45 mm.

Figure 14:
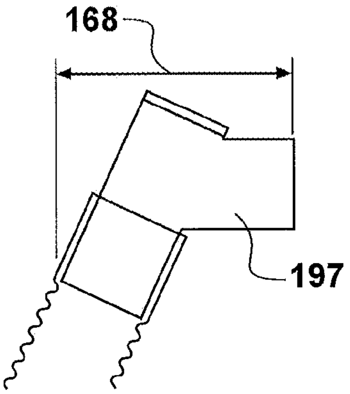
FIGS. 14-16 are side views illustrating example dimensions of various connectors and bypass adaptors in accordance with at least one embodiment of the present disclosure.
Figure 15:
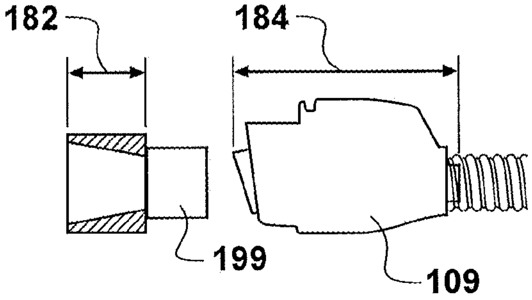
Figure 16:
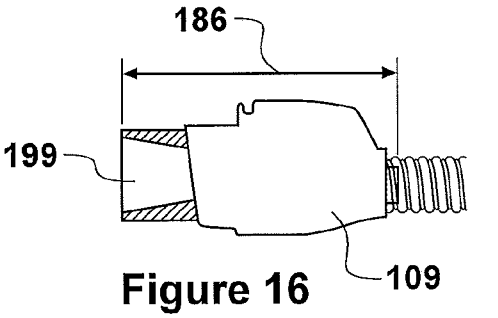

FIGS. 14 to 16 illustrate the problem created by the mounting arrangement of the humidification device 107 in close proximity to the ventilator 105 when using the inspiratory connector 109. FIG. 14 shows that the older inspiratory connector 197 comprises a width 168 of about 68 mm. Since the width 168 is smaller than the gap 148 between the lower portion of the rear edge of the humidification device 107 and the front edge of the filter 179, the older inspiratory connector 197 fits into the gap 148. FIG. 15 shows that the inspiratory connector 109 comprises a length 184 of about 70 mm, and a bypass adaptor 199 comprises a minimum protruding length 182 of about 21 mm. As shown in FIG. 16, when the bypass adaptor 199 is connected to the inspiratory connector 109, the resulting assembly has a length 186 of about 91 mm. Since the length 186 is larger than the gap 148, the assembly of the inspiratory connector 109 and the bypass adaptor 199 does not fit into the gap 148. These measurements correspond to the connection failures exhibited in the photographs of FIGS. 10 and 11.

Figure 17:
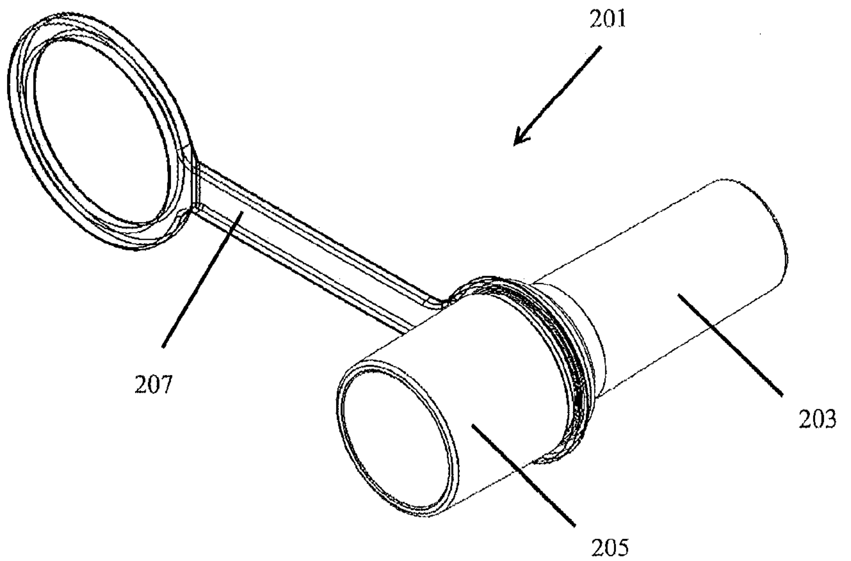
FIGS. 17-22 are perspective views of various bypass adaptors in accordance with at least one embodiment of the present disclosure, configured to connect an inspiratory conduit connector to a source outlet of a ventilator or to a supply conduit.

FIG. 17 shows an example embodiment of a bypass adaptor 201 in accordance with at least one embodiment of the present disclosure configured to connect the inspiratory connector 109 to the filter 179. As illustrated, the bypass adaptor 201 comprises a first connector comprising a source plug 205 configured to taper fit within the filter 179, a second connector comprising an inspiratory plug 203 configured to taper fit within the port plug 175 of the inspiratory connector 109, and a conduit or tube retainer 207 configured to attach to the inspiratory conduit 103. In some embodiments, the source plug 205 is configured to taper fit onto the outside of the source outlet 137. The tube retainer 207 may be useful to ensure that the bypass adaptor 201 is not lost before or after use. The tube retainer 207 comprises a ring through which, for example, the inspiratory conduit 103 can pass, such that the tube retainer 207 retains the bypass adaptor 201 on the inspiratory conduit 103. In some embodiments, the bypass adaptor 201 does not include a tube retainer.

Figure 18:
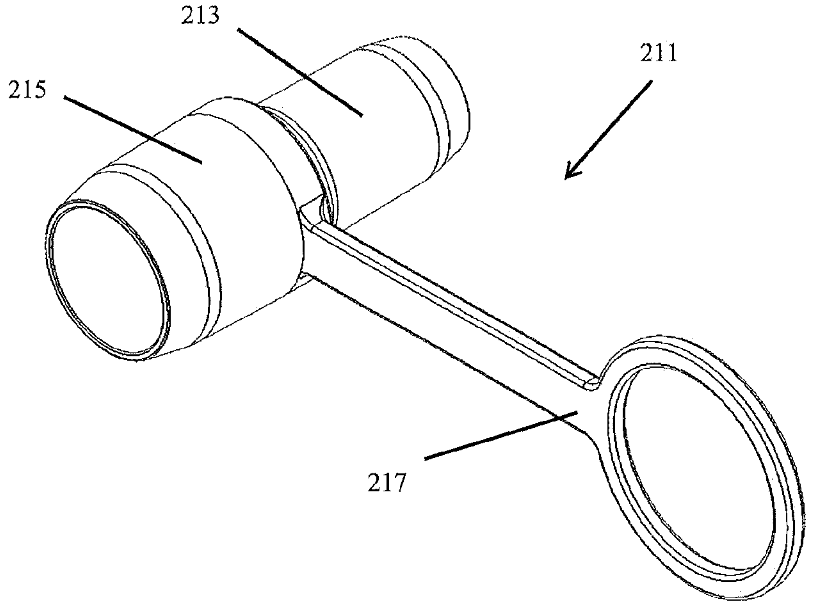

FIG. 18 shows an example embodiment of a bypass adaptor 211 configured to connect the inspiratory connector 109 to the filter 179. As illustrated, the bypass adaptor 211 comprises a first connector comprising a source plug 215 configured to push fit within the filter 179, a second connector comprising an inspiratory plug 213 configured to push fit within the port plug 175 of the inspiratory connector 109, and a tube retainer 217 configured to attach to the inspiratory conduit 103. In some embodiments, the source plug 215 is configured to push fit onto the outside of the source outlet 137. In some embodiments, the bypass adaptor 211 does not include a tube retainer.

Figure 19:
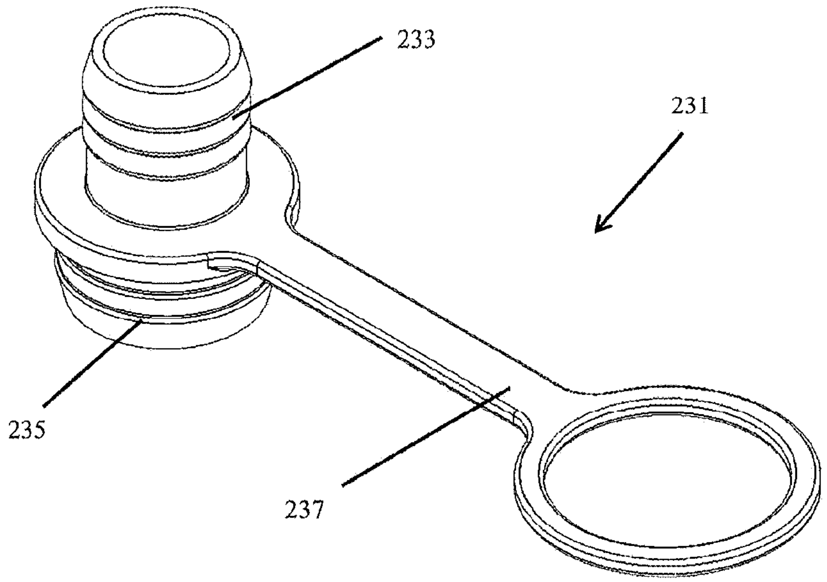

FIG. 19 shows an example embodiment of a bypass adaptor 231 configured to connect the inspiratory connector 109 to the filter 179. As illustrated, the bypass adaptor 231 comprises a first connector comprising a source plug 235 comprising multiple tapers configured to friction fit within the filter 179, a second connector comprising an inspiratory plug 233 comprising multiple tapers configured to friction fit within the port plug 175 of the inspiratory connector 109, and a tube retainer 237 configured to attach to the inspiratory conduit 103. In some embodiments, the bypass adaptor 231 does not include a tube retainer.

Figure 20:
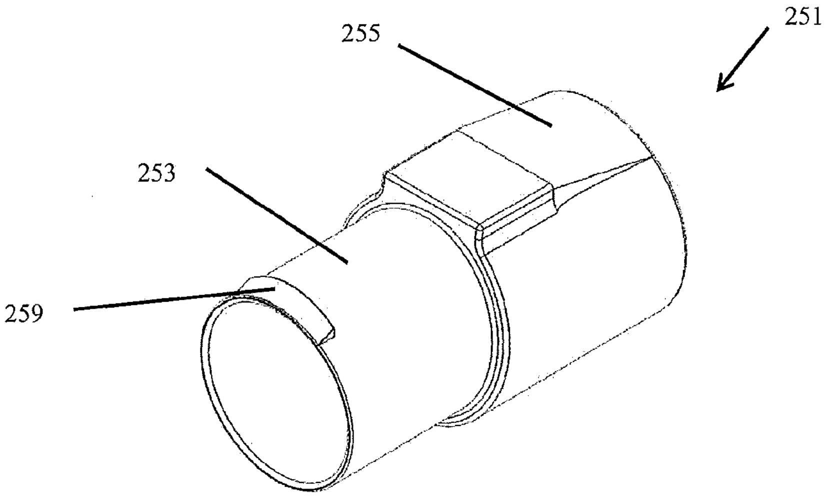

FIG. 20 shows an example embodiment of a bypass adaptor 251 configured to connect the inspiratory connector 109 to the filter 179. As illustrated, the bypass adaptor 251 comprises a first connector comprising a source plug 235 configured to taper fit around the outside of the filter 179 and a second connector comprising an inspiratory plug 253 comprising a locking ridge 259 configured to lockably fit within the port plug 175 of the inspiratory connector 109. In some embodiments, the bypass adaptor 251 includes a tube retainer.

The bypass adaptors 201, 211, 231, 251 are illustrated as comprising hollow bodies comprising first and second ends in fluid communication via a generally straight internal gas passageway. In other words, each of the first connectors, that is the source plugs 205, 215, 235, 255, defines a gas passageway that shares a common axis with a gas passageway defined by each of the second connectors, that is, the inspiratory plugs 203, 213, 233, 253, respectively. In these examples, the longitudinal axes of the first and second ends of the adaptors are coaxial. However, the first end is different from the second end in some physical respect, the first end having characteristics that enable it to be connected only to the source outlet 137 or filter 179, the second end having characteristics that enable it to be connected only to the inspiratory conduit 103. The characteristics that differ may be overall shape of the first and second tubular ends, the external diameter, the internal diameter and/or the degree of tapering of each end.

In some configurations, the physical constraints created by a mounting arrangement of the humidification device 107 in close proximity to the ventilator 105 may make it impracticable or impossible to use a bypass adaptor having first and second ends linked by a straight internal gas passageway, such as one of the bypass adaptors 201, 211, 231, 251. A bypass adaptor with an angled body may overcome this problem.

Figure 21:
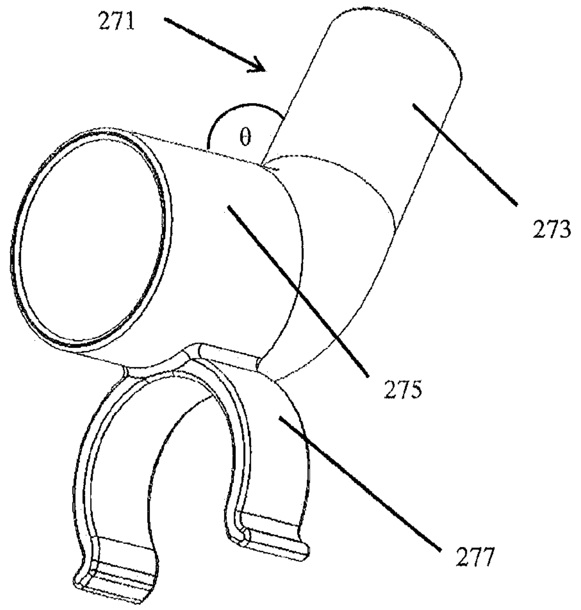
Figure 22:
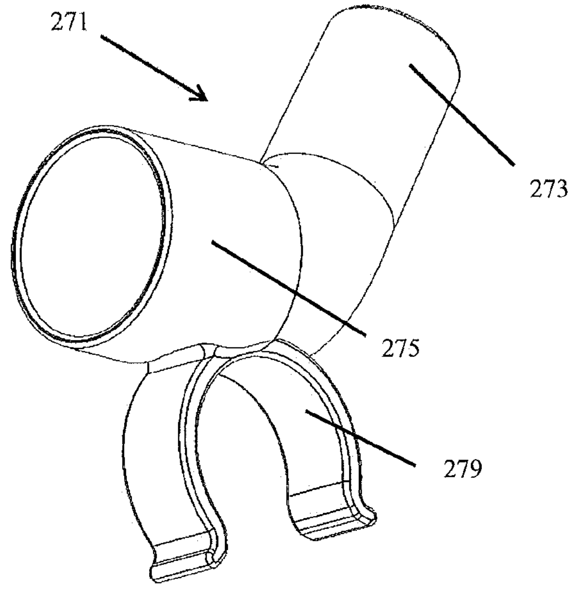
Figure 23:
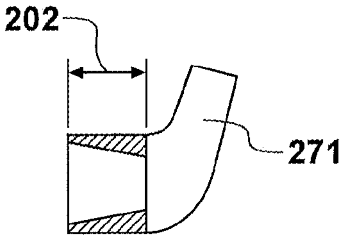
FIGS. 23-24 are side views illustrating example dimensions of various connectors and bypass adaptors in accordance with at least one embodiment of the present disclosure, with FIG. 23 being part sectional.
Figure 24:
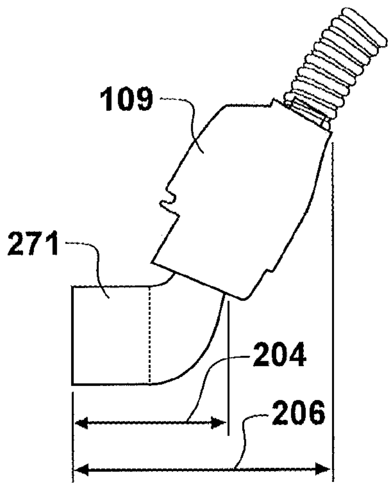

FIGS. 21 to 22 show an example embodiment of a bypass adaptor 271 configured to connect the inspiratory connector 109 to the filter 179. As illustrated in FIG. 21, the bypass adaptor 271 comprises a first connector comprising a source plug 275 configured to taper fit around the outside of the filter 179, a second connector comprising an inspiratory plug 273 configured to taper fit within the port plug 175 of the inspiratory connector 109, and a conduit or tube retainer 277 configured to attach to the inspiratory conduit 103 to retain the bypass adaptor 271 on for example the inspiratory conduit 103. In some embodiments, the bypass adaptor 271 does not include a tube retainer.

FIG. 22 shows an embodiment of the bypass adaptor 271 comprising a tube retainer 279 that is oriented 90 degrees away from the orientation of the tube retainer 277. The source plug 275 and the inspiratory plug 273 each comprise elongate tubular bodies having a respective longitudinal axis. The source plug 275 defines an internal gas passageway that does not share a common axis with the gas passageway defined by the inspiratory plug 273. Instead, the bypass adaptor 271 comprises an angle θ between the axis of the source plug 275 and the axis of the inspiratory plug 273. This allows the assembly of the inspiratory connector 109 connected to the bypass adaptor 271 to fit into the gap 148 between the rear and top of the humidification device 107 and the forward projecting end of the source outlet 137 or the filter 179, if provided. Thus the longitudinal axis of the first connector 275 is inclined relative to the longitudinal axis of the second connector 273. In some configurations, the angle θ is an obtuse angle and may for example be between about 110 degrees and about 160 degrees. In some configurations, the angle θ is between about 110 degrees and about 145 degrees. In some configurations, the angle θ is about 112 degrees.

Figure 25A:
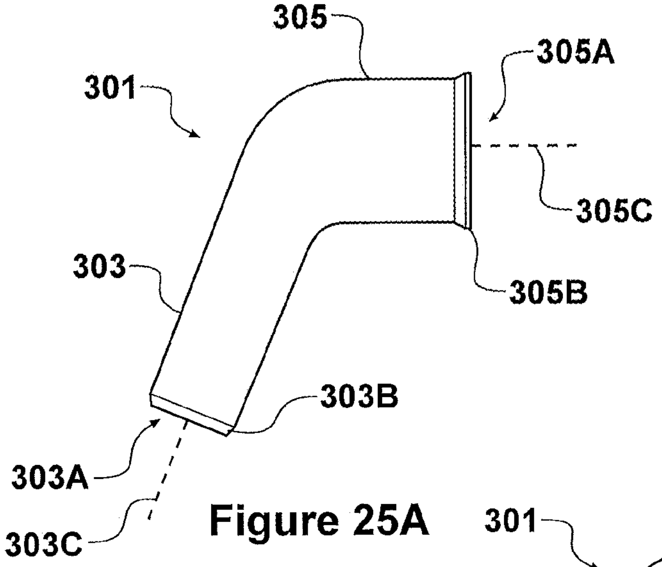
FIGS. 25A and 25B are side and perspective views respectively of a bypass adaptor in accordance with at least one embodiment of the present disclosure.
Figure 25B:
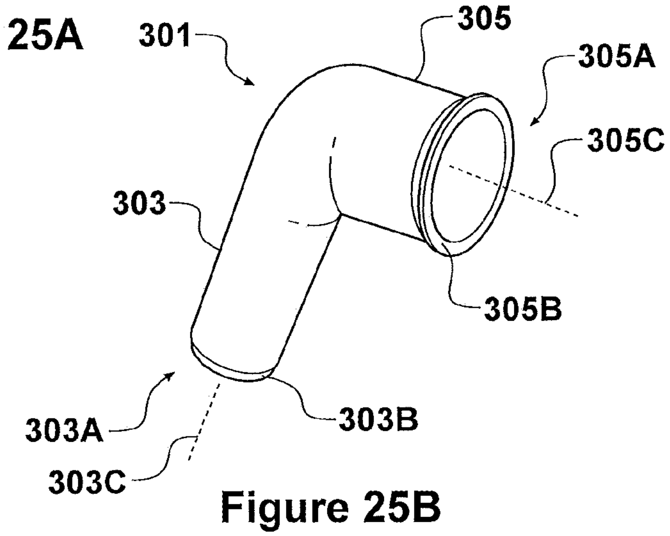

With reference to FIGS. 25*a* and 25*b*, a further bypass adaptor 301 in accordance with at least one embodiment of the present disclosure comprises a first elongate tubular connector end comprising a source plug 305 configured to taper fit around the outside of the filter 179 or source outlet 137, a second elongate tubular connector end comprising an inspiratory plug 303 configured to taper fit within the port plug 175 of the inspiratory connector 109. The first connector end 305 is relatively short, and tapers radially outwardly towards a relatively large aperture 305A. A radially outwardly flared lip 305B extends around the periphery of the aperture 305A. The second connector end 303 is relatively long and comprises a shallow, radially inwardly taper towards a relatively small aperture 303A. A radially inwardly directed chamfer 303B extends around the periphery of the aperture 303B. The longitudinal axis 305C of the first connector end 305 is not aligned with, but intersects, the longitudinal axis 303C of the second connector end 303 at an obtuse angle of around 112 degrees. The first connector end 305 is thus configured for connection only to the source outlet 137 or the filter 179, whilst the second connector end 303 is configured for connection only to the connector 109 of the inspiratory conduit 103. The radiused and chamfered ends can help prevent incorrect connection of the bypass adaptor 301 to other parts of the respiratory assistance system 100, and particularly to the inspiratory conduit 103.

Figure 26A:
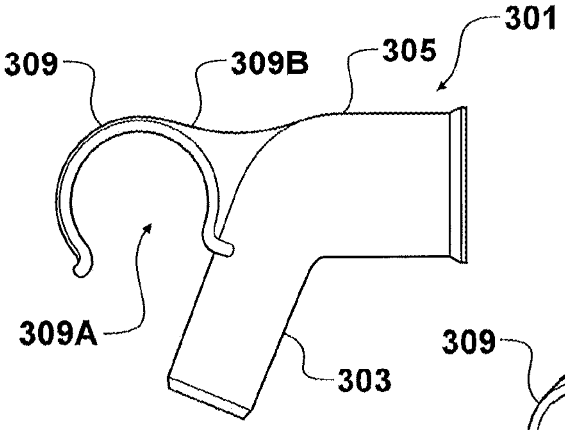
FIGS. 26A and 26B are side and perspective views respectively of another bypass adaptor in accordance with at least one embodiment of the present disclosure.
Figure 26B:
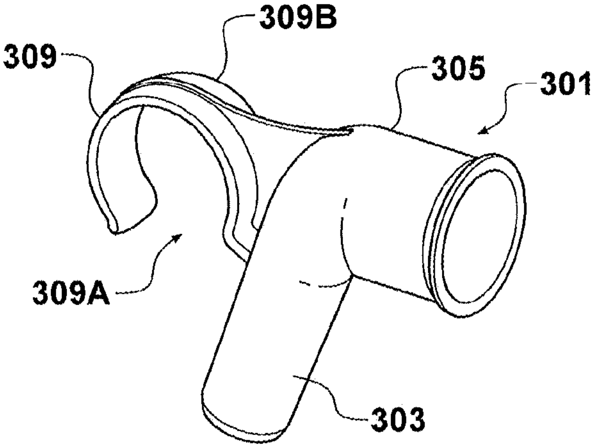

With reference to FIGS. 26*a* and 26*b*, a modification of the further bypass adaptor 301 comprises a tube or conduit retainer 309 in the form of a spring clip having a mouth 309A into which, for example, the inspiratory conduit 103 may be received, the mouth 309A deflecting outwardly as the inspiratory conduit 103 is pressed into the retainer 309 and subsequently springing back to its non-deflected condition to engage and retain the inspiratory conduit 103. In this example, the tube retainer 309 extends from the narrower part of the hollow body of the bypass adaptor 301 adjacent the intersection of the first and second connector ends 305, 303, and is partially connected to the hollow body by a web 309B. This configuration enables the tube retainer 309 to additionally function as a hand grip or handle to enable the bypass adaptor 301 to be easily picked up and manipulated. When so held, the narrower part of the hollow body and the second connector end 303 also facilitate holding the bypass adaptor 301, and facilitate pushing the first connector end 305 onto the outlet source 137 or the filter 179.

The embodiments of the bypass adaptors 201, 211, 231, 251, 271, 301 described above are intended to be illustrative and not limiting. Other combinations and arrangements of aspects of the bypass adaptors 201, 211, 231, 251, 271, 301 are possible and are to be included in the scope of this disclosure. As an example, a bypass adaptor may comprise a closed or ring-shaped tube retainer as illustrated by the tube retainers 207, 217, 237, an open-ended or horseshoe-shaped tube retainer as illustrated by the tube retainers 277, 279, 309, or no tube retainer. In these latter examples, the tube retainers 277, 279 may be resiliently deformable so as to provide a spring clip which deforms as a conduit, for example the inspiratory conduit 103, is pressed into the tube retainer and then springs back to grip and retain the bypass adaptor on the inspiratory conduit 103. Each of the tube retainers 207, 217, 237, 277, 279, 309 may be attached to a bypass adaptor at a different angle, in a different orientation, or to a different attachment point than illustrated. For example, the longitudinal axes of the first and second tubular connector ends of the bypass adaptor may be parallel but not coaxial, so that one tubular connector end is laterally spaced from the other tubular connector end.

Other tube retainer designs that are configured to fit on or around a breathing tube or other respiratory system component may also be used. As another example, any one of the source plugs 205, 215, 235, 255, 275, 305 may be combined in a bypass adaptor with any one of the inspiratory plugs 203, 213, 233, 253, 273, 303. Also, any one of the source plugs 205, 215, 235, 255, 275, 305 may be configured to fit within or around the filter 179 or the source outlet 137. Thus the first and/or second ends of the bypass adaptors may comprise sockets configured to receive the source outlet 137 and the inspiratory conduit 103 for example. These alternative arrangements and combinations of aspects of the bypass adaptors 201, 211, 231, 251, 271, 301 are intended only to be examples and are not limiting.

In some configurations, the humidification device 107 may be bypassed while leaving the supply conduit 151 connected to the ventilator 105, by disconnecting the humidification device connector 153 of the supply conduit 151 from the inlet port 159, disconnecting the inspiratory connector 109 from the outlet port 111, and connecting the inspiratory connector 109 to the humidification device connector 153 using the bypass adaptor 201, 211, 231. The source plug 205, 215, 235 may be sized to fit within the humidification device connector 153 or around the humidification device connector 153.

In some embodiments, the ventilator 105 includes a self-test function. The ventilator 105 of such an embodiment may require the self-test to be conducted with the humidification device being bypassed, that is, without, humidified gas being supplied to the respiratory assistance system 100. The bypass adaptors 201, 211, 231, 251, 271, 301 provide an adaptor having first and second end connectors, shaped, sized, tapered and with longitudinal axes orientated in such a way that the inspiratory conduit 103 can be connected directly to the source outlet 137, with or without an optional intermediate filter 179, in the very limited vertical and horizontal space provided between the humidification device and the ventilator 105.

The generally straight bypass adaptors 201, 211, 231, 251 may be configured to connect the supply conduit 151 to the source outlet 137 or filter 179. The angled bypass adaptors 271, 301 may be configured to form a direct connection between one end of the inspiratory conduit 103 and the source outlet 137 or filter 179. The angled bypass adaptors 271, 301 are configured such that the connectors are not aligned and do not share the same vertical plane. Thus one connector is vertically spaced below the other connector. A straight line between one connector and the other is shorter than the length of the gas flow path between the connectors. These properties make the bypass adaptors 271, 301 relatively short when viewed from the side, facilitating their use in the relatively short space between the ventilator 105 and the humidification device.

The bypass adaptors 201, 211, 231, 251, 271, 301 may be provided with visual indicia configured to distinguish the bypass adaptors 201, 211, 231, 251, 271, 301 from other components of the respiratory assistance system 100. For example, other conduits and connectors of the respiratory assistance system 100 may be of a transparent or semi-transparent material, whilst the bypass adaptors may be of a contrasting solid and/or coloured material for example. This may assist in highlighting the bypass adaptors 201, 211, 231, 251, 271, 301 as not being for normal use of the respiratory assistance system 100, and/or as being disposable items.

In accordance with at least one embodiment of the present disclosure, there is provided a conduit kit 401 for the respiratory assistance system 100 comprising the inspiratory conduit 103 and the bypass adaptor 201, 211, 231, 251, 271, 301 as described above, the inspiratory conduit 103 configured to be connected between the patient interface 115 and the humidification device 107.

The conduit kit 401 may further comprise any one or more of: (a) the supply conduit 151, configured to be connected between the ventilator 105 and the humidification device 107; (b) the conduit connector 109, configured to form a connection with one end of the inspiratory conduit 103; (c) the expiratory conduit 117; (d) the humidification chamber 129; (e) a wye-piece connector; (f) a filter for connection to the source outlet 137; and/or (g) at least one cap or plug for closing one or more of the inlets, outlets, or conduits of the system 100.

The conduit kit 401, or any of the components of the conduit kit 401, may be supplied in a sterilized form, and may be provided with one or more components in sealed, sterilized packets for example. Any one or more of the components of the conduit kit 401 may be arranged to be disposable after a single use. The bypass adaptors described above may, for example, be single use, and disposable thereafter.

Figure 27:
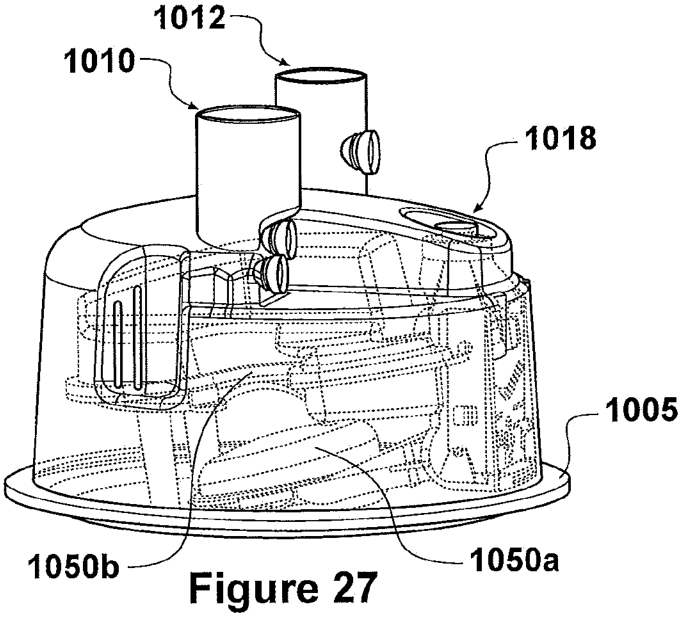
FIG. 27 shows an example humidification chamber and components thereof.
Figure 28A:
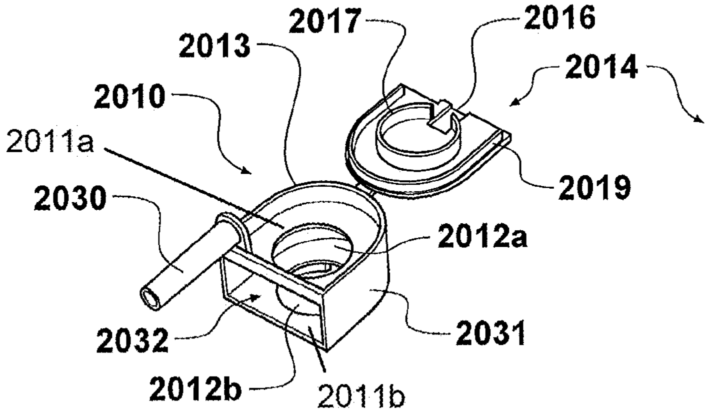
FIGS. 28A-28D provide various views of a port cap according to an embodiment of the invention.
Figure 28B:
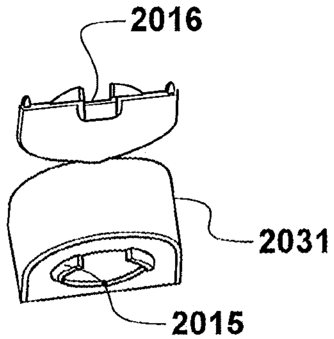
Figure 28C:
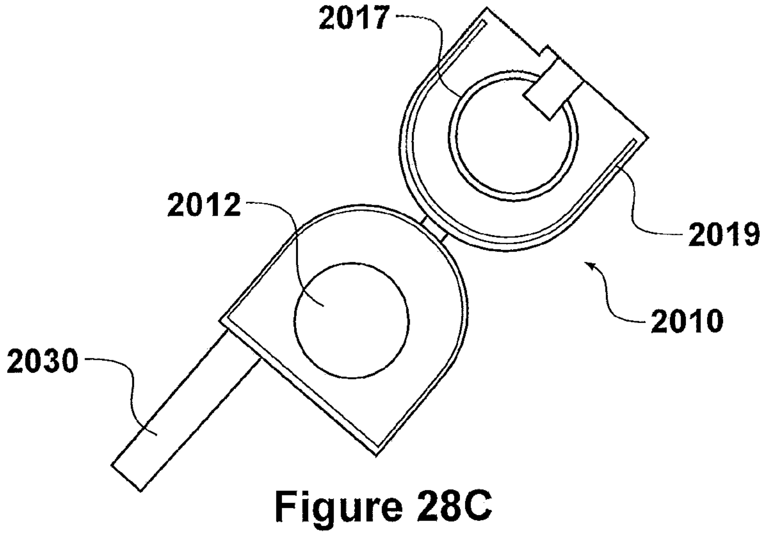
Figure 28D:
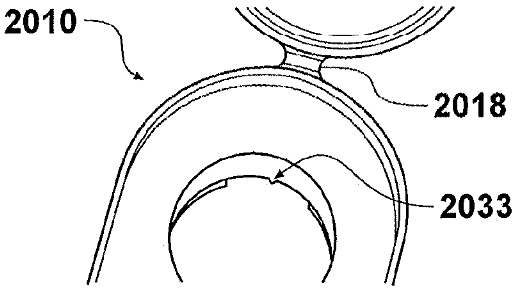
Figure 29A:
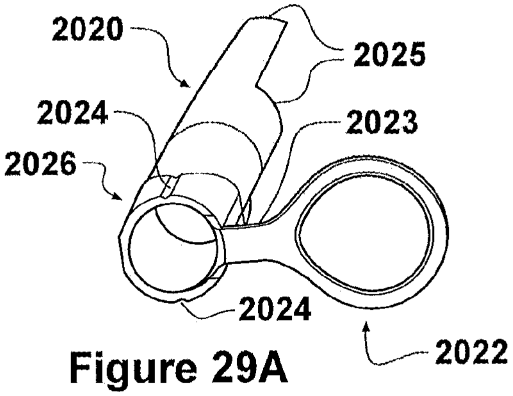
FIGS. 29A-29D provide various views of a leg according to an embodiment of the invention that is configured to be assembled with the port cap of FIGS. 28A-28D.
Figure 29B:
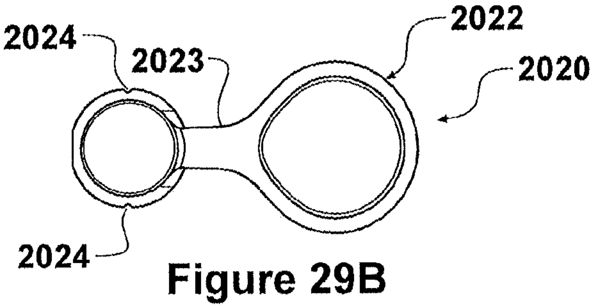
Figure 29C:
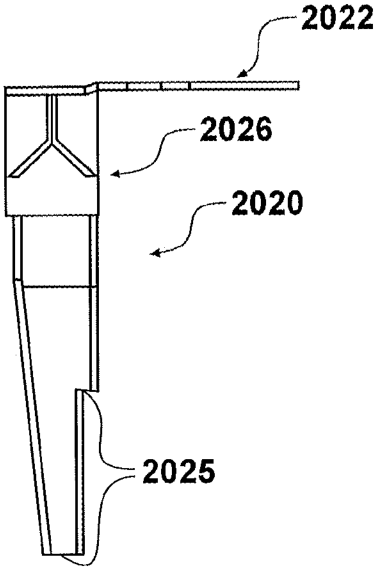
Figure 29D:
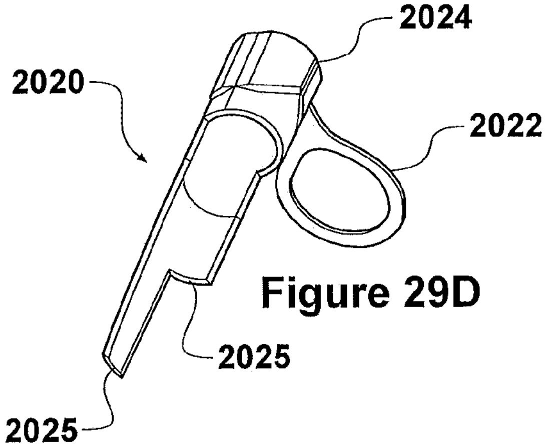

An example humidification chamber 1004 is shown in FIG. 27. The humidification chamber 1004 generally comprises an inlet 1010 and an outlet 1012 and is configured to be installed on a heater plate of a heater base of a humidification device, such as humidification device 107 of FIG. 1. The humidification chamber 1004 is configured to hold a volume of a liquid, such as water. The chamber 1004 can include an opening or port 1018 for the connection of a liquid conduit or feedset. The liquid conduit can extend from the chamber 1004. In some configurations, the liquid conduit can connect to a spike for a water bag. In some configurations, the liquid conduit can be integrally formed with or permanently coupled to the chamber 1004. The spike can be coupled to the liquid conduit via an adhesive, sonic welding, an interference fit, or any other suitable means. In some embodiments, the spike includes a vent. If the spike is inserted into, for example, a plastic, collapsible bag, the vent is plugged. However, if the spike is inserted into a rigid container, such as a glass bottle, the vent is open and allows air to enter the container to help reduce or prevent negative pressures in the container. The vent can include a filter that is permeable to gases but impermeable to liquids.

In use, the liquid conduit conveys a liquid, for example, water, from a liquid source, such as a water bag, saline bag, or the like, to the chamber 1004. The heater plate heats the chamber 1004 and causes at least some of the chamber 1004 contents to evaporate. In some embodiments, the humidification chamber 1004 can include features to help reduce the likelihood of the level of liquid in the chamber 1004 from exceeding a particular level. For example, the chamber 1004 can include one or more floats 1050.

The floats rise and fall with the level of liquid in the chamber 1004. When the liquid level reaches a certain level, the floats 1050 obstruct or block the port that is connected to the liquid conduit to stop or slow further ingress of liquid into the chamber 1004. Other similar features also can be used. In a preferred embodiment, a plurality of floats 1050 are used, each float adapted to stop the further ingress of liquid into the chamber 1004. To this end, a second float provides a backup or safety mechanism, thereby further reducing the likelihood of the chamber 1004 overfilling. FIG. 27 illustrates an example embodiment of such a chamber 104 having a primary float 1050*a* and a secondary float 1050*b*.

The chamber 1004 is configured to connect to a breathing circuit assembly which can include a supply conduit, an inspiratory conduit, and, in some configurations, an expiratory conduit. A gases supply end of the supply conduit is configured to connect to an output of a gases supply and a chamber end of the supply conduit is configured to connect to the inlet 1010 of the chamber 1004. A chamber end of the inspiratory conduit is configured to connect to the outlet 1012 of the chamber 1004, and a user end of the inspiratory conduit is configured to connect to the user via an interface, for example.

In use, gases flow from the gases supply through the supply conduit and into the chamber 1004 via the inlet 1010. The gases are humidified within the chamber 1004 and exit the chamber 1004 through the outlet 1012. The user inhales humidified gases supplied through the inspiratory conduit, and may exhale into the expiratory conduit. The inspiratory conduit and/or expiratory conduit can include a heating element, for example, a heating wire, to help maintain the gases at a desired temperature and to reduce the likelihood of significant condensation formation in the conduits.

Before use, an operator, such as medical personnel, must correctly connect the various components to set up the system. Because of the variety of components and number of connections that must be made, set-up of the system can be a complex process that requires special training to complete properly. The humidification system can include various features as described herein to simplify the set-up process and reduce the likelihood of an incorrect set-up. In some embodiments, certain usability features advantageously can help reduce the total number of steps and time required during the set-up process. Some features described herein also can help make set-up more intuitive for the user, which can reduce the need for specialized in-service training.

To begin set-up, the operator installs the humidification chamber 1004 on the heater base by sliding the chamber 1004 onto the heater base. Engagement features such as a rim edge on the heater base can help hold the chamber 1004 in place. The heater plate can be spring loaded in some configurations such that the base of the chamber 1004 presses downward upon the heater plate and a protruding portion 1005 of the chamber 1004 can be captured between the heater plate and the rim edge. Features may be provided to prevent unwanted or accidental removal of the chamber 1004 from the heater base. For example, a guard along a front portion of the rim edge may be provided that is depressed to enable the lower portion of the chamber 1004 to engage access the heater plate and then the guard reverts to a non-depressed position once the chamber 1004 is installed. This advantageously provides positive feedback that the chamber 1004 is fully installed on the base.

In some configurations, the forwardmost portions of the rim edge (e.g., the portions of the rim edge that define an opening for insertion of the chamber 1004) are configured with a raised or enlarged opening that ramps downward. The opening preferably comprises a lower surface that is elevated above an upper surface of the non-depressed guard. In such a manner, the opening provides a visual clue to the operator that the protruding portion 1005 can be inserted into the opening. Further insertion of the chamber 1004 into the opening causes the guard to be depressed and facilitates full insertion of the chamber into the heater base and can help guide the chamber 1004 into place. Thus, these visual details can indicate to the operator that the chamber 1004 slides into place under the rim edge. This can also help inform the operator that the guard can be depressed to later remove the chamber 1004 from the heater base. Preferably, the chamber 1004 has details to depress the guard when the operator attempts to remove the chamber 1004 from the heater base. Moreover, by providing an uneven upper surface to the rim edge, the operator is less likely to believe that the chamber 1004 should be placed atop the rim edge, resulting in poor thermal conductivity, because such a placement will lead to an uneven positioning of the chamber 1004.

The humidification chamber 1004 can be packaged with port caps covering the inlet 1010 and/or the outlet. The port caps can seal or generally enclose the chamber 1004 during shipping and storage. A port cap 2010 according to an embodiment of the invention is shown in FIGS. 28A-28D and is configured to engage with the leg 2020 of FIGS. 29A-29D to form a port cap assembly. In the illustrated embodiment, the leg includes a pull tab or loop 2022. The pull tab 2022 advantageously allows the user to remove the leg 2020 more easily during the appropriate stage of set-up. The pull tab 2022 is visually intuitive such that the user will typically understand that he or she is to pull on the pull tab 2022 without requiring additional instructions. When engaged with the port of the chamber 1004, the leg 2020 extends into the inlet 1010 and/or the outlet 1012 and restrains the float(s) 1050 in position for shipping. For further discussion of chamber arrangements, including floats and retention thereof, feedsets and example configurations of the broader humidification system, reference is again made to WO2015/174859, previously incorporated herein by reference.

The port cap 2010 has a first wall portion 2011*a* and a second wall portion 2011*b*, each having a respective aperture 2012*a*, 2012*b* therethrough that together define a passageway through the wall portions 2011*a*, 2011*b*. A flange extends away from the second wall portion 2011*a* to define a rim 2013. A lid 2014 is configured to engage the rim 2013. The passageway is configured to receive the leg 2020 therethrough such that it extends into the inlet 1010 (or outlet 1012) when the port cap assembly is engaged with the chamber port 1010, 1012. The apertures 2012*a*, 2012*b* are arranged and/or configured to control an orientation of the leg 2020 relative to the port 2012*a*, 2012*b*. For example, as shown in the drawings, the apertures 2012*a*, 2012*b* may be dimensioned and shaped substantially the same as at least an outer profile or surface of the portions of the leg 2020 received therein, but slightly larger to accommodate said portions without excessive force being required. Consequently, movement of the leg 2020 is preferably restricted once fully inserted such that it can only move in a direction aligned with the passageway, and when attached to the chamber, the port 1010, 1012.

The port cap assembly can include other or additional orientation and/or alignment features. For example, the port cap 2010 can include one or more projections or recesses that engage one or more corresponding recesses or projections associated with the port (preferably provided on an external wall of the port) so as to control a rotational orientation of the port cap relative to the inlet port about an axis through the passageway and/or the port 1010, 1012. For example, in the embodiment shown, the port cap 2010 includes projections 2015, configured to be received either side of a rib provided on an external wall of the port 1010, 1012 to prevent rotation thereof. The rib on the port 1010, 1012 can further act as a stop to limit the extent to which the cap 2010 can be inserted onto the port 1010, 1012 by the rib on the port coming into abutment with the lower edge of the cap 2010 between the projections 2015. Additionally or alternatively a projection such as projection 2033 (see FIG. 28D) can engage a slot in an external wall of the port 1010, 1012. As will be appreciated, the projecting features such as projections 2015, 2033 or a rib on the port may be interchanged with the recessed features such as grooves or slots.

The lid 2014 of the port cap 2010 can be configured to engage the leg 2020. For example, one or more projections or recesses provided on the lid 2014 may engage one or more corresponding recesses or projections on the leg 2020 to control a position and/or orientation thereof. One or more such recesses or projections on the lid 2014 can be configured to engage a wall defining the leg 2020 without separate or additional means provided on the leg 2020 to enable engagement. For example, in the embodiment shown, the notch 2016 is configured to receive a portion of the pull tab 2022, more particularly, the arm 2023 linking the pull tab 2022 to the leg 2020. Further, the projection 2017 provided on the underside of the lid 2014 is configured to be received inside the leg 2020, with the projection 2017 in abutment with the inner wall of the leg 2020 at the end thereof provided with the pull tab 2022. While projection 2017 is shown depending from the lid and providing continuous wall other than at the notch 2016, it may be otherwise configured. For example, the wall may be discontinuous and/or vary in height.

The leg 2020 can include other or alternative orientation and/or alignment features, and or intrinsically provide therefor. According to one embodiment, at least a portion of the leg 2020 is dimensioned so as to fit snugly inside the port 1010, 1012, thereby controlling an alignment of the leg 2020 with respect to the port 1010, 1012. Additionally or alternatively, the leg 2020 can include one or more projections or recesses that engage one or more corresponding recesses or projections associated with the port 1010, 1012 (preferably provided on an internal wall of the port) so as to control a rotational orientation of the leg 2020 relative to the port 1010, 1020 about an axis through the passageway or port. For example, in the embodiment shown, grooves 2024 are configured to receive projections or ribs provided on an inner wall of the port 1010, 1012.

The leg 2020 can be configured to secure one or more floats within the chamber 1004 for shipping and/or storage. To this end, the leg 2020 can define or have one or more engagement points 2025, each engagement point 2025 being configured to engage a respective float and retain the float in a particular position when the port cap assembly is installed on the chamber 1004. Further details of this engagement and the structure of the leg are provided in WO2015/174859, previously incorporated herein by reference.

According to the illustrated embodiment, the leg 2020 comprises a generally cylindrical portion at or near a first end which preferably tapers towards the second end by portions of the cylinder effectively being cut away or removed and/or the diameter of the cylinder reducing towards the second end. As shown, preferably, the cylindrical portion 2026 is hollow such that the first end of the leg 2020 is open. This particular attribute and the separation of the leg 2020 from the port cap 2010 is a distinction over the arrangements disclosed in WO2015/174859. This arrangement intuitively confers to an operator that the leg 2020 and the port cap 2010 should not be re-connected to the port 1010, 1012 after initial removal. Tapering can aid insertion of the leg through the passageway and into the port of the chamber. Cut-outs and the like perform a similar function but can also assist in enabling proper insertion of the leg 2020 into the chamber 1004 as well as providing for the required engagements with the float(s).

As disclosed in WO2015/174859, the chamber 1004 may include a baffle that defines an arcuate profiled passageway inside the chamber 1004. Preferably, this arcuate profile is complementary to the profile of the portion of the leg 2020 that passes therethrough when the port cap 2010 and leg 2020 are engaged with the port 1010, 1012 of the humidification chamber 1004. By forming the leg 2020 profile to be complementary to the arcuate passageway, the leg 2020 and arcuate wall or passageway can cooperate to control a rotational position of the leg 2020 inside the port and/or the orientation thereof such that the leg 2020 is generally aligned with the port 1010, 1012. Further, the baffle can assist in preventing liquid in the chamber 1004 from spilling as the chamber 1004 is transported and control flow of gases into the chamber 1004, providing for more effective humidification.

The lid 1014 can be connected to a main body of the port cap 1010 via a hinge 1018. As shown, this hinge 1018 may be in the form of a flexible arm of, for example, polymer-based material, that may be integrally formed with or fixedly joined to the lid 1014 and the main body of the port cap 1010, preferably at or proximate the rim 2013. However, the hinge 2018 may be omitted in which case the lid 2014 may be detachable. The lid 2014 may be configured to engage the rim 2013 with a snap- or friction- or other type of fit.

The lid 2014 can further comprise a projection 2019 that engages the inside or outside of the rim 2013 to provide for improved connection and retention of the lid in a closed position of engagement on the main body of the port cap 2010. Alternatively, a depression could be provided in the lid 2014, the depression being configured to receive the rim 2013 therein.

The port cap assembly can comprise a sleeve 2030 for receiving and removably retaining a spike which may be provided with a water or other humidifying agent feedset. For example, the spike may be coupled or couplable to a delivery conduit that is coupled or couplable to the humidification chamber 1004. The sleeve 2030 can be connected to a main body of the port cap 2010, preferably at or adjacent the rim 2013

The sleeve 2030 and/or the profile of the port cap 2010 with opposing straight and arced walls can assist initial assembly of the port cap assembly to the chamber 1004 by providing visual indicators of the required orientation of the components.

The port cap 2010 can include a joining wall 2031 extending between the first and second wall portions 2011*a*, 2011*b*, preferably at or near the perimeters or edges of the wall portions 2011*a*, 2011*b*. The joining wall 2031 can extend beyond the second wall portion 2011*b* to provide said flange and rim 2013. At least one opening or window 2032 can be provided in the joining wall 2031 such that the joining wall 2031 does not extend completely about the perimeters or edges of the wall portions 2011*a*, 2011*b*. When the leg 2020 is assembled or engaged to the port cap 2010, the joining wall 2031, the first and second wall portions 2011*a*, 2011*b* and a portion of the leg 2020 can define a space for accommodating at least a portion of flexible tubing for use in a humidifying agent feedset. More particularly, at least one end of feedset tubing coils may be received in said space with the leg 2020 then being inserted into the passageway to retain the coils in position. A portion of the coils may extend out through the opening or window 2032 such that the coils wrap about the leg 2020.

To assemble the port cap assembly to the chamber 1004, the port cap 2010 may first be slid into engagement with the port 1010, 1012, then the leg 2020 slid into engagement inside the port 1010, 1012 and the lid 2014 closed. Alternatively, the leg 2020 may first be slid into the passageway. Preferably, the lid 2014 is then closed such that the orientation of the leg 2020 relative to the port cap 2010 is controlled. The sub-assembly 2010, 2020 is then slid into engagement with the port 1010, 1012. Where the port cap is provided with a feedset, coils of the tubing therefor may be inserted into the opening 2032 as a pre-step, before the above steps and as a final step, a spike of the feedset can be inserted into the sleeve 2030.

To remove the port cap assembly from the chamber 1004, an operator pulls on the pull tab 2022 and removes the leg 2020. The port cap 2010 can then be removed and any feedset tubing and spike detached from the port cap 2010. If an operator does then replace the port cap 2010 onto the port 1010, 1012, it is unlikely they would also insert the leg 2020 which can help prevent damage caused by the leg 2020 to components inside the chamber 1004 e.g. grommets covering sensor ports into the chamber 1004. Alternatively the entire port cap assembly may be removed from the chamber 1004 in one step, with the leg 2020 then being removed by pulling on the pull tab 2022 to enable removal of feedset items.

Since the feedset tubing is coiled at least partially in the port cap until the leg is removed, a user is substantially prevented from connecting the feedset to a water bag or other reservoir until the leg is removed. This is advantageous as the floats are "deactivated" with the leg in position and so overfilling of the chamber can be prevented.

Figure 30:
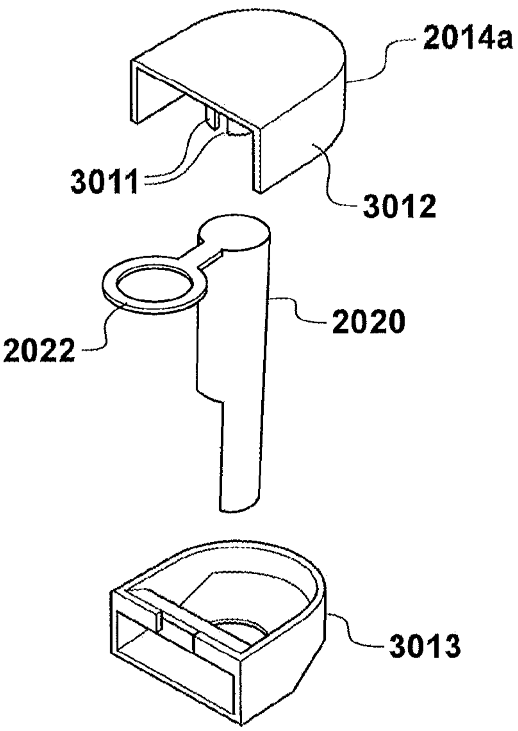
FIG. 30 is an exploded view of a port cap assembly according to an embodiment of the invention.

A modified version of the embodiment of FIGS. 28A-29D is shown in FIG. 30. In view of the similarity, only distinguishing features of this embodiment will be described. As can be seen in FIG. 30, the lid 2014 differs. According to this embodiment, rather than being hinged, the lid 2014*a* is loosely associated the remainder or main body 3013 of the port cap. For example, downwardly depending first wall(s) 3011 are sized to be received within and/or about a chamber port. The first wall(s) 2014*a* may engage the chamber port and/or the leg 2020 and/or the main body 3013 of the port cap via a loose fit or some, preferably low force, retention features may be provided. For example, there may be a bump or friction fit. Further, downwardly depending second wall(s) 3012 are sized to be received about the remainder of the port cap or the port cap main body 3013. The second wall(s) 3012 may engage the main body 3013 via a loose fit or some, preferably low force, retention features may be provided. For example, there may be a bump or friction fit. The forces required to remove the lid/port cap should be low to ensure easy removal by pulling the pull tab 2022. Either of the first and second walls 3011, 3012 may be omitted. According to the embodiment of FIG. 30, a user is likely to retain only the lid 2014*a* and place this over the chamber port, thereby providing a dust cover when the chamber is not in use.

Figure 31:
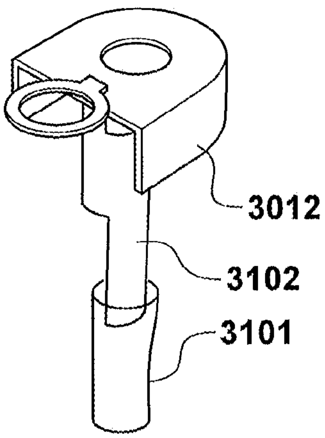
FIG. 31 is a perspective view of at least a part of a port cap assembly according to an embodiment of the invention.

A further alternative embodiment is shown in FIG. 31. According to this embodiment an end portion 3101 of the leg comprises or is formed from a foam or some other resiliently pliable material. Preferably, the end portion extends a length sufficient to prevent the more rigid base portion 3102 of the leg from abutting or contacting grommets or the like that may be provided to sensor ports in the chamber. The grommets may, for example, include a wall defining a dome with a skirt depending therefrom (i.e. generally bell-shaped). Near the end of the skirt remote from the dome, means may be provided to retain the grommet in the aperture in the port. For example, a slot may be provided wherein the wall of the port about the aperture is received inside the slot. The invention is not limited to such embodiments but this arrangement is preferred as it provides for easy initial installation as well as subsequent removal and replacement. The grommets may be formed from an elastic material such as a silicon or rubber. In order for sensors positioned inside the grommets to provide accurate readings, the sensors preferably abut the dome-shaped part of the grommets. Further, the sensors preferably exert force on the dome parts, stretching the wall of the dome and reducing its thickness, further improving accuracy. This also provides tolerance for the fits of the sensors or sensor probes inside the grommets. As a consequence, the grommets may be relatively delicate. Forming an end portion of the leg from a foam can obviate damage to and/or dislodgement of grommets by avoiding relatively rigid members abutting against the grommets and/or sensors and/or probes. Note that this form of grommet may be applied across all embodiments requiring a sensor or sensor probe to be provided in breathable gases flow path.

The end portion is preferably sufficiently resilient to retain the floats in position but sufficiently pliable or deformable such that no damage any grommets or the like. The port cap assembly of FIG. 31 may otherwise be configured per the embodiment of FIG. 30 i.e. the base and end portions 3102 and 3103 that form the leg may removably engage the lid portion 3012 and/or main body 3013.

A further embodiment is shown in FIGS. 32A-32E. According to this embodiment, the pull tab or ring 3202 is provided on a first side of the port cap 3201. The port cap 3201 includes a skirt or downwardly depending wall 3203. The downwardly depending wall or skirt 3203 is omitted or includes a cut-out at least at a second side of the port cap 3201. The second side opposes or substantially opposes the first side of the port cap 3201. The leg 3204 is joined to the port cap 3201 but the port cap 3201 preferably includes a weakened area 3205 at or proximate part of the join between the port cap 3201 and the leg 3204.

Figure 32A:
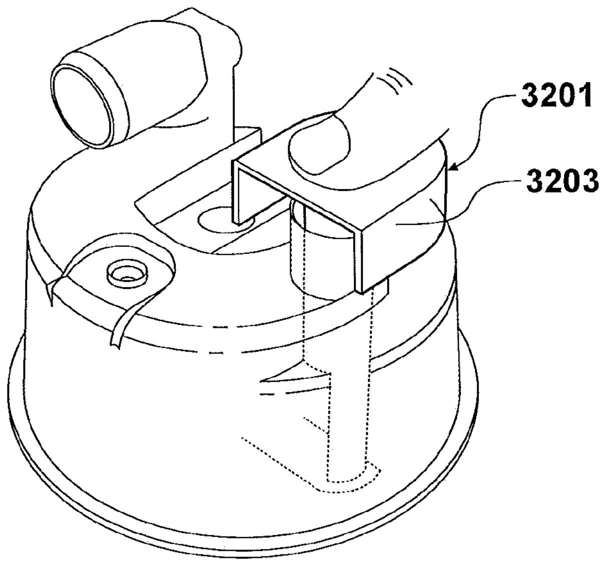
FIGS. 32A-32E provide various views of at least a part of a port cap assembly according to an embodiment of the invention.
Figure 32B:
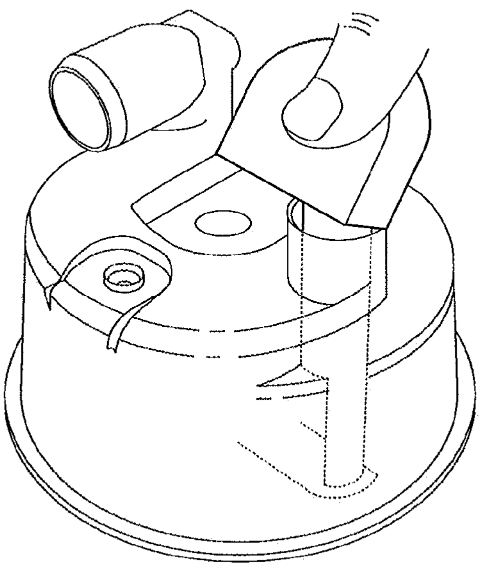
Figure 32C:
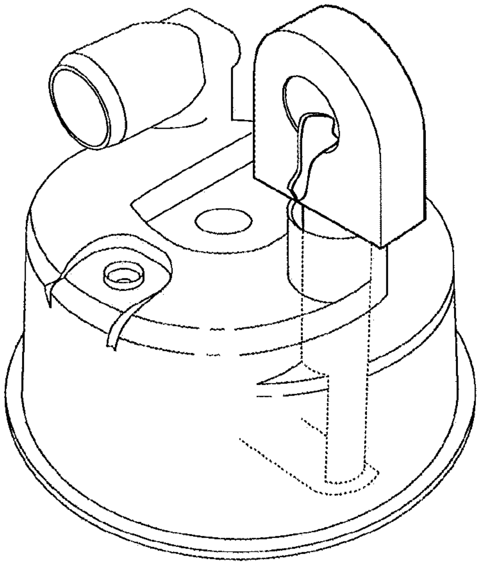
Figure 32D:
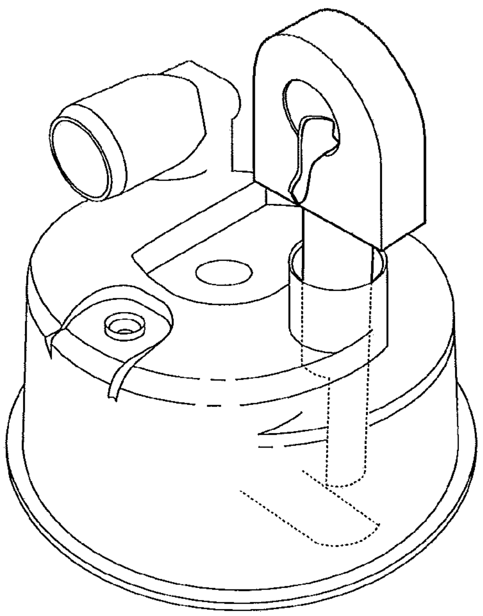
Figure 32E:
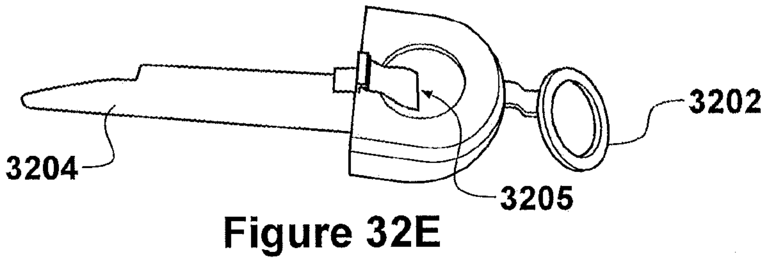

As can be seen from the sequence shown in FIGS. 32A-32E, a user grips the pull tab (FIG. 32A). As the user pulls upwardly, the port cap 3201 begins to tilt (FIG. 32B), this being made possible by attachment of the pull tab or ring on an opposing side of the port cap to the cut-out in the skirt 3203. Further pulling causes the weakened area to break and the upper part of the port cap tilts further (FIG. 32C). The tilting means that continued pulling of the tab is in a direction along the longitudinal axis of the chamber port such that further pulling (32D) removes the port cap 3201 and leg 3204 from the chamber port. The removed port cap 3201 and leg 3204 is shown in FIG. 32E. Since the port cap 3201 is now irreparably damaged, it is intuitive to a user that it should be discarded, preventing any damage caused by reinsertion of the leg into the chamber.

Figure 33:
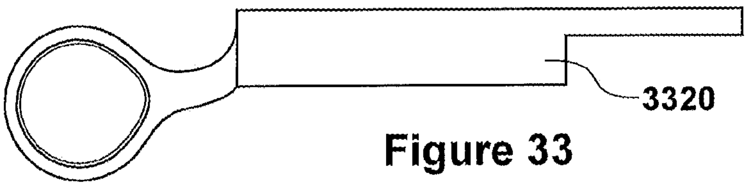
FIGS. 33 and 34 provide views of legs according to embodiments of the invention, for a port cap assembly.

FIG. 33 shows an alternative embodiment of a leg 3320 that may be used with other embodiments of the invention such as those shown in FIGS. 28A-29D. According to this embodiment, the circumference of the leg has been reduced to reduce the likelihood that it will shear against and dislodge or damage a grommet for a sensor and/or a sensor. Additionally or alternatively, the width or circumferential extent of the leg may be reduced, also reducing the likelihood of damage to components of the humidification chamber.

Figure 34:
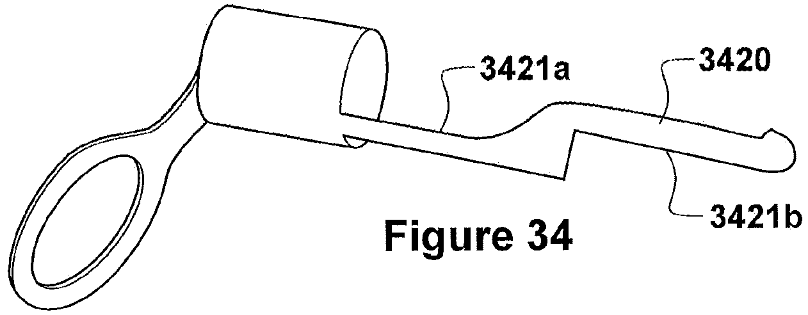

FIG. 34 shows an alternative embodiment of a leg 3420 that may be used with other embodiments of the invention such as those shown in FIGS. 28A-29D. According to this embodiment, portions 3421*a*, 3421*b* of the leg have been removed so as to weaken the leg and reduce its width, thereby reducing the likelihood that it will shear against and dislodge or damage a grommet for a sensor and/or a sensor.

A further alternative embodiment of a leg 3520 is shown in FIGS. 35A-35D. According to this embodiment. the leg 3520 is formed from a relatively, thin flexible plastic member that has a fold 3521 along its length to provide rigidity. The leg further includes pull tab 3522. This arrangement may be used with a port similar to that shown in FIGS. 28A-29D. The flexible nature of the leg inherently aids in reducing the likelihood of damage to components of the humidification chamber by any reinsertion of the leg into the chamber since the leg will tend to deform on impact of the leg against any external surface. Further, the low cost appearance and disposable-type nature of the leg gives users an inherent impression that the object is disposable, thereby reducing the likelihood of reinsertion at all. The low cost and/or disposable-type appearance may be applied to other components of the port cap assembly.

Figure 35A:
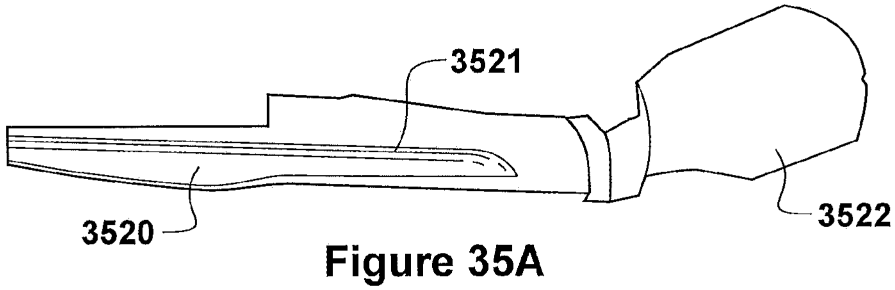
FIG. 35A shows a leg according to an embodiment of the invention and FIGS. 35B-35D provide various views of that the leg of FIG. 35A being removed from a wider port cap assembly according to an embodiment of the invention.
Figure 35B:
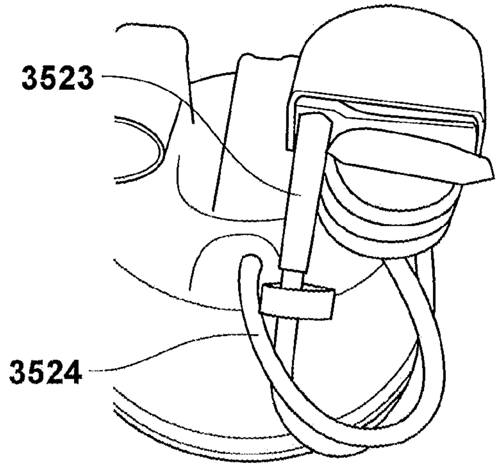
Figure 35C:
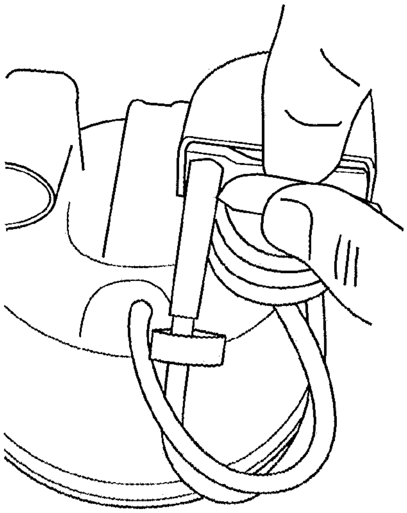
Figure 35D:
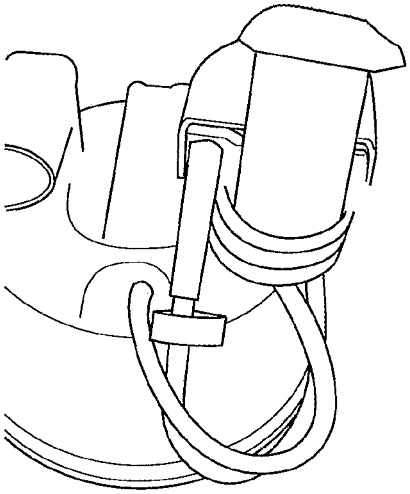

FIG. 35B shows the port cap assembly of this embodiment assembled with a chamber. As shown, the humidifying liquid (e.g. water) feed line 3524 is shown coiled around the leg 3520 and housed within the main body of the port cap with a sleeve 3523 retaining a spike of the feed line 3524. The sleeve prevents the spike from being able to puncture the liquid reservoir, or otherwise couple thereto FIG. 35C shows the first step of removal of the leg with a user gripping the pull tab 3522. On continued pulling, the lid is removed and then the leg 3520 (see FIG. 35D). Due to the configuration of the leg 3522, reinsertion is difficult and a user would not be inclined to reinsert the member in any event due to its inherent nature of appearing to be disposable. Further, in the event that a user were to reinsert the leg 3522 into the chamber port, its flexibility means that the likelihood of damage to a grommet and/or sensor is diminished.

Figure 36:
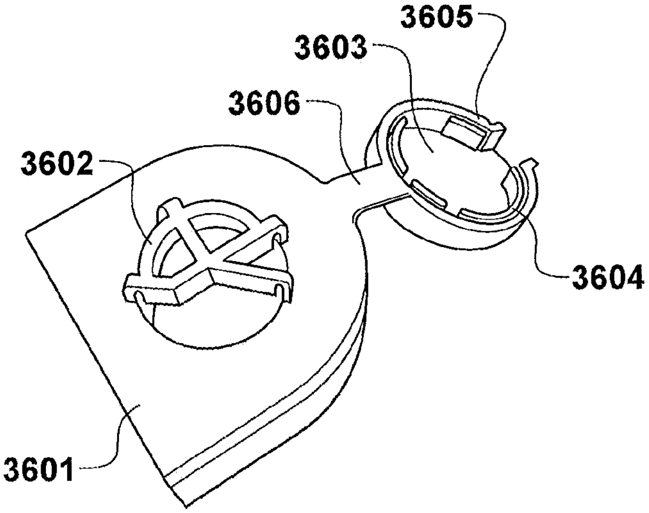
FIG. 36 shows a port cap according to an embodiment of the invention.

FIG. 36 shows an alternative embodiment of a port cap 3601 that may be used with arrangements similar to those shown in FIGS. 28A-29D. According to this embodiment, one or more additional wall portions or members 3602, that may together form a lattice, are provided so as to define a restricted passageway, blocking insertion of the leg other than in a preferred orientation, namely a rotational orientation of the leg about the passageway and/or a longitudinal axis of the chamber port. For example, as shown in FIG. 36, the members may define a wider spacing in one part than another part, such as by providing for a wider spacing between two members or a first member and a wall defining the passageway, than another pair of said members or the first or another member and a wall defining the passageway. The wider spacing can act as a visual indicator as to where to insert the leg. The narrower gap between other members is preferably less than a width of the leg and may be less than a thickness or profile thickness or cross-sectional shape of the leg. Consequently, damage to a grommet and/or a sensor may be avoided by only allowing insertion of the leg in a predetermined orientation that is offset from the grommet and/or sensor. Another distinguishing feature of the embodiment of FIG. 36 is that the lid 3603 is of a reduced size, commensurate with the size of the passageway defined in the port cap 3601. First wall portions 3604 are provided that releasably but fixedly join the lid to the main body of the port cap 3601. Second wall portions 3605 provide a cleaner finish to the lid 3603 and prevent contamination to the chamber such as via dust etc. One or other of the first and second wall portions may be omitted and engagement of the lid with the main body of the port cap 3601 may alternatively be via the second wall 3605. Engagement may be via a friction or bump fit or any other equivalent, with the engagement preferably requiring a relatively low force for disengagement so that the lid is easily opened and the leg is easily removed from the port cap 3601. Note that the leg of this embodiment is preferably a separate part, such as that shown in FIG. 34.

The arm joining the lid 3603 to the main body of the port cap 3601 of this, and all other embodiments, may include a weakened portion 3606, allowing the lid 3603 to be detached from the port cap 3601. According to such embodiments, the lid may be attachable to the port of the chamber to prevent contamination thereto via dust, etc.

Figure 37A:
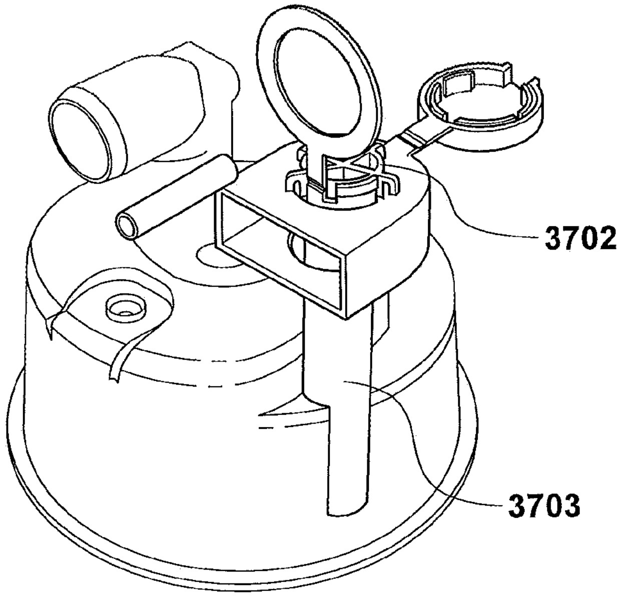
FIGS. 37A and 37B show alternative views of an embodiment of a port cap assembly connected to a humidification chamber.
Figure 37B:
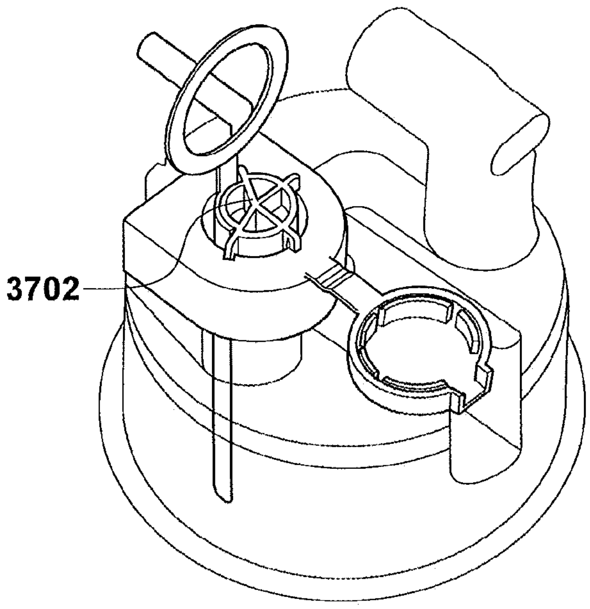

FIGS. 37A and 37B show a slightly modified version of the embodiment of FIG. 36. According to this embodiment, the members 3702 define a more restricted passageway, further limiting the permitted orientation of the leg 3703 upon insertion.

Figure 38A:
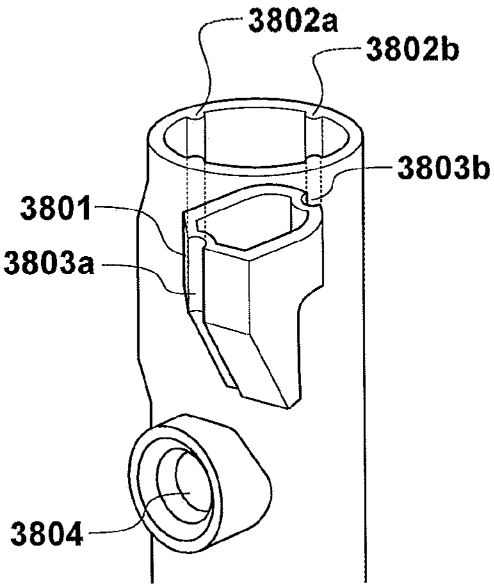
FIGS. 38A and 38B show inserts according to alternative embodiments of the invention.
Figure 38B:
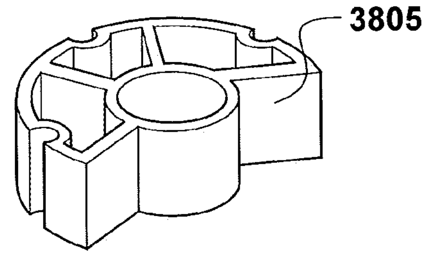

FIGS. 38A and 38B show alternative embodiments wherein restriction of the passageway and/or port to provide for a preferred orientation of the leg upon insertion is provided via an insert provided inside the port. Similar to the embodiment of FIG. 36, wall portions or members define a restricted passageway, such as via a lattice. As with other embodiments, the restricted passageway may define an opening having substantially the same shape as the end profile of the leg.

According to the embodiment of FIG. 38A, the insert 3801 engages ribs or protrusions 3802*a* and 3802*b* via channels 3803*a* and 3803*b*, respectively. Again the ribs and channels may be interchanged. The insert 3801 serves as a shield, protecting the grommet and/or sensor extending through the aperture 3804. More particularly, as shown, the insert is configured or shaped to deflect or direct the leg away from the grommet and/or sensors or otherwise act as a physical barrier between the grommet and/or sensor and the leg.

FIG. 38B shows an alternative configuration of an insert 3805, similar to that of insert 3801 of FIG. 38A.

The above described embodiments of the port cap assembly that control an orientation of the leg upon insertion not only help to protect against damage to the grommet and/or sensor by reinsertion but also during initial assembly prior to shipment thereof.

As will be apparent to those skilled in the art, such apparatus is ordinarily originally supplied in sealed packaging. To avoid damage to that packaging, in particular puncturing thereof, preferably, the port cap assembly is configured to avoid sharp edges and protrusions when assembled to a chamber for shipment. For example, rounded corners and edges may be provided on any external edges or corners of the assembly such as around the sleeve and/or the gripping portion and/or protruding elements may be configured to be flexible.

It should be understood that any examples used in this description are in no way limiting, but merely illustrative of possible embodiments for purposes of clarification. Unless the context clearly requires otherwise, throughout this description and the claims that follow, the words "comprise", "comprising", and the like, are to be construed in an inclusive sense as opposed to an exclusive or exhaustive sense, that is to say, in the sense of "including, but not limited to".

Reference to any prior art in this description is not, and should not be taken as, an acknowledgement or any form of suggestion that the prior art referenced forms part of the common general knowledge in any relevant field of endeavour in any country in the world.

The present invention may be said broadly to consist in the parts, elements, and features referred to or indicated in this description and the claims that follow, individually or collectively, in any or all combinations of two or more of said parts, elements, or features. Where reference is made to integers or components having known equivalents thereof, those equivalents are herein incorporated as if individually set forth.

It should be noted that various modifications to the embodiments disclosed herein will be apparent to those skilled in the art. Such modifications may be made without departing from the spirit and scope of the present invention and without diminishing its attendant advantages. For instance, various components may be repositioned or reshaped as desired. It is therefore intended that such modifications be included within the scope of the invention. Moreover, not all of the features, aspects, and advantages disclosed herein are necessarily required to practice the present invention. Accordingly, the scope of the present invention is intended to be defined only by the claims that follow.

What is claimed is:

1. A respiratory assistance system comprising:

an inspiratory conduit;

an expiratory conduit;

a humidification chamber;

a cap configured to close one or more of an inlet, an outlet, or a conduit of the respiratory assistance system; and a bypass adaptor that is not connectable to the humidification chamber, the bypass adaptor being configured to enable the inspiratory conduit to be connected between a gases source and the cap such that the humidification chamber can be bypassed, the bypass adaptor comprising:

an inlet connector configured to be directly and removably connected to an outlet of the gases source and configured to not connect to an outlet of the humidification chamber or to a connector of the inspiratory conduit;

an outlet connector configured to be directly and removably connected to a connector of the inspiratory conduit and configured to not connect to an outlet of the gases source or to the outlet of the humidification chamber; and a hollow body defining a gas flow path between the inlet connector and the outlet connector, wherein the inlet connector is different from the outlet connector in at least an external diameter or an internal diameter.

2. The respiratory assistance system of claim 1, wherein a shape of the inlet connector is different from a shape of the outlet connector.

3. The respiratory assistance system of claim 1, wherein each of the inlet connector and the outlet connector is tubular.

4. The respiratory assistance system of claim 1, wherein a length of the inlet connector is different from a length of the outlet connector.

5. The respiratory assistance system of claim 1, wherein at least one of the inlet connector and the outlet connector tapers along its length.

6. The respiratory assistance system of claim 5, wherein each of the inlet connector and the outlet connector comprises a taper, and the taper on the inlet connector is different from the taper on the outlet connector.

7. The respiratory assistance system of claim 1, wherein each of the inlet connector and the outlet connector is elongate and has a longitudinal axis, the longitudinal axis of the inlet connector is at an obtuse angle relative to the longitudinal axis of the outlet connector.

8. The respiratory assistance system of claim 7, wherein the obtuse angle between the longitudinal axis of the inlet connector from the longitudinal axis of the outlet connector is between about 110 degrees and about 160 degrees.

9. The respiratory assistance system of claim 7, wherein the obtuse angle between the longitudinal axis of the inlet connector from the longitudinal axis of the outlet connector is about 112 degrees.

10. The respiratory assistance system of claim 1, further comprising a retainer such that the bypass adaptor can be retained on or to the inspiratory conduit or another component of the respiratory assistance system when not connected to the outlet of the gases source.

11. The respiratory assistance system of claim 10, wherein the retainer comprises a ring through which the inspiratory conduit or a second conduit is received or a spring clip defining a variable size mouth configured to receive the inspiratory conduit or the second conduit, the variable size mouth being biased to a condition in which the variable size mouth retains the inspiratory conduit.

12. The respiratory assistance system of claim 1, further comprising a supply conduit configured to be connected between the gases source and the humidification chamber.

13. The respiratory assistance system of claim 1, further comprising:

an interface connector configured to form a connection between an end of the inspiratory conduit and the cap; and an expiratory conduit.

14. The respiratory assistance system of claim 1, wherein the bypass adaptor is configured to enable the gases source to conduct a test without the humidification chamber connected.

15. The respiratory assistance system of claim 1, wherein the bypass adaptor comprises a hollow body defining an internal gas passageway that extends from a first end to a second end, the inlet connector positioned at the first end of the hollow body and the outlet connector positioned at the second end of the hollow body.

16. The respiratory assistance system of claim 15, wherein the hollow body of the bypass adaptor does not comprise a valve.

17. The respiratory assistance system of claim 1, wherein the bypass adaptor has only two connectors, which are the inlet connector and the outlet connector.

* * * * *